(12) United States Patent
Saylor et al.

(10) Patent No.: US 9,013,574 B2
(45) Date of Patent: Apr. 21, 2015

(54) MACHINE VISION SYSTEM PROGRAM EDITING ENVIRONMENT INCLUDING SYNCHRONIZED USER INTERFACE FEATURES

(71) Applicant: Mitutoyo Corporation, Kawasaki-shi, Kanagawa-ken (JP)

(72) Inventors: Barry Saylor, Kent, WA (US); Ryan Northrup, Renton, WA (US); Akira Takada, Yokohama (JP); Kozo Ariga, Koutou (JP)

(73) Assignee: Mitutoyo Corporation, Kawasaki-shi (JP)

( * ) Notice: Subject to any disclaimer, the term of this patent is extended or adjusted under 35 U.S.C. 154(b) by 400 days.

(21) Appl. No.: 13/676,061

(22) Filed: Nov. 13, 2012

(65) Prior Publication Data

US 2013/0125044 A1 May 16, 2013

Related U.S. Application Data

(63) Continuation-in-part of application No. 13/297,232, filed on Nov. 15, 2011, now Pat. No. 8,957,960.

(60) Provisional application No. 61/560,278, filed on Nov. 15, 2011.

(51) Int. Cl.
*G06F 3/00* (2006.01)
*G06F 9/44* (2006.01)
(Continued)

(52) U.S. Cl.
CPC .............. *G06F 8/38* (2013.01); *G01N 21/8851* (2013.01); *G06F 9/4443* (2013.01); *G05B 19/409* (2013.01); *G05B 19/4093* (2013.01);
(Continued)

(58) Field of Classification Search
None
See application file for complete search history.

(56) References Cited

U.S. PATENT DOCUMENTS 4,835,730 A 5/1989 Shimano
5,481,712 A 1/1996 Silver
(Continued)

OTHER PUBLICATIONS

"QVPAK 3D CNC Vision Measuring Machine: Operation Guide," Version 2.0, Manual No. 4911GB, Series No. 359, Mitutoyo Corporation & Micro Encoder Inc., Kanagawa, Japan, Sep. 1996, 86 pages.
(Continued)

*Primary Examiner* — Joseph Ustaris
*Assistant Examiner* — William Adrovel
(74) *Attorney, Agent, or Firm* — Christensen O'Connor Johnson Kindness PLLC

(57) ABSTRACT

A machine vision system program editing environment including synchronized selection and/or identification of related features in a plurality of different user interface windows is provided. In particular, one of the windows is an editing window where a part program representation is displayed for editing by a user. In one embodiment, a user may select data or another feature of interest in a window that is not the editing window (e.g., a results window, or graphical workpiece inspection feature display window) and the associated part program instruction representation is automatically highlighted and/or selected in the editing window. Conversely, a part program instruction representation may be selected by a user in the editing window and the associated results or feature in another window is automatically highlighted and/or selected. User interface navigation, rapid program quality assessment, and overall part program creation and editing efficiency are significantly enhanced in such an editing environment.

18 Claims, 21 Drawing Sheets

(51) Int. Cl.
*G06F 9/45* (2006.01)
*G06F 3/048* (2013.01)
*G05B 19/409* (2006.01)
*G05B 19/4093* (2006.01)
*G01N 21/88* (2006.01)

(52) U.S. Cl.
CPC .............. *G05B2219/35505* (2013.01); *G05B 2219/36143* (2013.01); *G05B 2219/36172* (2013.01); *G05B 2219/37208* (2013.01); *G05B 2219/37439* (2013.01); *G05B 2219/37455* (2013.01); *Y10S 715/964* (2013.01); *Y10S 715/97* (2013.01); *Y10S 715/965* (2013.01)

(56) References Cited

U.S. PATENT DOCUMENTS

| | | | |
|---|---|---|---|
| 5,537,546 A | 7/1996 | Sauter |
| 6,016,467 A | 1/2000 | Newsted |
| 6,510,434 B1 | 1/2003 | Anderson |
| 6,542,180 B1 | 4/2003 | Wasserman |
| 6,636,211 B2 | 10/2003 | Chartier |
| 7,055,092 B2 | 5/2006 | Yardumian |
| 7,207,017 B1 | 4/2007 | Tabery |
| 7,324,682 B2 | 1/2008 | Wasserman |
| 7,376,904 B2 | 5/2008 | Cifra |
| 7,454,053 B2 | 11/2008 | Bryll |
| 7,590,276 B2 | 9/2009 | Delaney |
| 7,643,907 B2 | 1/2010 | Fuhlbrigge |
| 7,689,634 B2 | 3/2010 | Agarwal |
| 7,864,178 B2 | 1/2011 | Marini |
| 8,028,085 B2 | 9/2011 | Elien |
| 8,111,905 B2 | 2/2012 | Campbell |
| 8,111,938 B2 | 2/2012 | Bryll |
| 2006/0150148 A1 | 7/2006 | Beckett |
| 2006/0178778 A1 | 8/2006 | Fuhlbrigge |
| 2007/0067290 A1 | 3/2007 | Makela |
| 2007/0150102 A1 | 6/2007 | Park |
| 2007/0250204 A1 | 10/2007 | Ould |
| 2009/0164202 A1 | 6/2009 | Lönnemark |
| 2010/0103679 A1 | 4/2010 | Lee |
| 2010/0158343 A1 | 6/2010 | Bryll |
| 2010/0269094 A1 | 10/2010 | Levenshteyn |
| 2011/0103679 A1 | 5/2011 | Campbell |
| 2013/0120553 A1 | 5/2013 | Delaney |
| 2013/0120567 A1 | 5/2013 | Northrup et al. |

OTHER PUBLICATIONS

"QVPAK 3D CNC Vision Measuring Machine: User's Guide," Version 7.1, 2d ed., Manual No. 99MCB225A, Series No. 359, Mitutoyo Corporation & Micro Encoder Inc., Kanagawa, Japan, Sep. 2003, 370 pages.

```
<DefineLine breakpoint="FALSE" nodeID="{C9A83BEB-3A17-4D98-9DEB-C964FC5F1D82}" returnCode="MIML_OK" blockMarker="FALSE" simulationStatus="good">
    <featureLabel>line-2</featureLabel>
    <x>127.8935842</x>
    <y>184.8642784</y>
    <z>10.7407000</z>
    ...
</DefineLine>
```

805 ← (pointing to the code block)
810 ← (bracing the x, y, z lines)
800 (figure identifier)

Fig. 8.

```xml
<Measure breakpoint="FALSE" nodeID="{B4969AD8-FE38-4F4D-A9C9-9A445082CBDA}" returnCode="MIML_OK" blockMarker="FALSE" simulationStatus="good">
    <ImageSetContext breakpoint="FALSE" nodeID="{C6C9D82A-F67A-4D07-8394-72236F4AB5AE}" returnCode="MIML_OK" blockMarker="FALSE" simulationStatus="good">
        <x>1.998521000</x>
        <y>1.998199531</y>
        <z>-0.002600000</z>
        <coax>0</coax>
    </ImageSetContext>
    <BoxTool breakpoint="FALSE" nodeID="{0197EFDA-BE83-45B3-AFAF-B0C47E4D2BC5}" returnCode="MIML_OK" blockMarker="FALSE" simulationStatus="good">
        <vcs>FALSE</vcs>
        <x>2.310565547</x>
        <y>2.000848736</y>
        <z>-0.002700000</z>
        <w>0.196030000</w>
        <h>0.574280300</h>
        <standardDetection>
            <step1>
                <addDetectN1>0</addDetectN1>
                <addDetectD1>0.000000000</addDetectD1>
                <addDetectD2>0.000000000</addDetectD2>
                <addDetectD3>0.000000000</addDetectD3>
                <addDetectD4>0.000000000</addDetectD4>
            </step1>
        </standardDetection>
```

```xml
<filterType>@</filterType>
    <dllName>@</dllName>
    <paramList>@</paramList>
    <scanInterval>20</scanInterval>
    <samplingDirection>LEFT</samplingDirection>
<simulationData>
    <SimDataPoints>
        <SimDataPoint type="xyz" x="2.5845592668924591" y="1.9996700697272411" z="-0.0026000000000010461"/>
        <SimDataPoint type="xyz" x="2.5453539842250821" y="1.9995709619830411" z="-0.0026000000000010461"/>
        <SimDataPoint type="xyz" x="2.5061586571484661" y="1.9999918328428643" z="-0.0026000000000010461"/>
        <SimDataPoint type="xyz" x="2.4669588355058511" y="1.9997869543609261" z="-0.0026000000000010461"/>
    </SimDataPoints>
</simulationData>
</BcxTool>
<DefineLine breakpoint="FALSE" nodeID="{C9A833BEB-3A17-4D9B-8DEB-C964FC5F1D82}" returnCode="MiML_OK" blockMarker="FALSE" simulationStatus="good">
    <featureLabel>L3</featureLabel>
    <x>2.310158654</x>
    <y>1.999734885</y>
    <z>-0.002600000</z>
</DefineLine>
</Measure>
```

*Fig. 17B.*

MACHINE VISION SYSTEM PROGRAM EDITING ENVIRONMENT INCLUDING SYNCHRONIZED USER INTERFACE FEATURES

CROSS-REFERENCE TO RELATED APPLICATIONS

This application claims the benefit of and priority from U.S. Provisional Patent Application No. 61/560,278, filed Nov. 15, 2011, and U.S. patent application Ser. No. 13/297,232, filed Nov. 15, 2011.

FIELD OF THE INVENTION

The invention relates generally to machine vision inspection systems, and more particularly to methods for creating and editing part programs in such systems.

BACKGROUND

Precision machine vision inspection systems (or "vision systems" for short) can be utilized to obtain precise dimensional measurements of inspected objects and to inspect various other object characteristics. Such systems may include a computer, a camera and optical system, and a precision stage that is movable in multiple directions so as to allow the camera to scan the features of a workpiece that is being inspected. One exemplary prior art system that is commercially available is the QUICK VISION® series of PC-based vision systems and QVPAK® software available from Mitutoyo America Corporation (MAC), located in Aurora, Ill. The features and operation of the QUICK VISION® series of vision systems and the QVPAK® software are generally described, for example, in the *QVPAK 3D CNC Vision Measuring Machine User's Guide*, published January 2003, and the *QVPAK 3D CNC Vision Measuring Machine Operation Guide*, published September 1996, each of which is hereby incorporated by reference in their entirety. This product, as exemplified by the QV-302 Pro model, for example, is able to use a microscope-type optical system to provide images of a workpiece at various magnifications, and move the stage as necessary to traverse the workpiece surface beyond the limits of any single video image. A single video image typically encompasses only a portion of the workpiece being observed or inspected, given the desired magnification, measurement resolution, and physical size limitations of such systems.

Machine vision inspection systems generally utilize automated video inspection. U.S. Pat. No. 6,542,180 teaches various aspects of such automated video inspection and is incorporated herein by reference in its entirety. As taught in the '180 patent, automated video inspection metrology instruments generally have a programming capability that allows an automatic inspection event sequence to be defined by the user for each particular workpiece configuration. This can be implemented by text-based programming, for example, or through a recording mode which progressively "learns" the inspection event sequence by storing a sequence of machine control instructions corresponding to a sequence of inspection operations performed by a user with the aid of a graphical user interface, or through a combination of both methods. Such a recording mode is often referred to as "learn mode" or "training mode." Once the inspection event sequence is defined in "learn mode," such a sequence can then be used to automatically acquire (and additionally analyze or inspect) images of a workpiece during "run mode."

Video tools (or "tools" for short) and other graphical user interface features may be used manually to accomplish manual inspection and/or machine control operations (in "manual mode"). Their set-up parameters and operation can also be recorded during learn mode, in order to create automatic inspection programs, or "part programs." Video tools may include, for example, edge/boundary detection tools, autofocus tools, shape or pattern matching tools, dimension measuring tools, and the like. Other graphical user interface features may include dialog boxes related to data analysis, step and repeat loop programming, and the like. For example, such tools are routinely used in a variety of commercially available machine vision inspection systems, such as the QUICK VISION® series of vision systems and the associated QVPAK® software, discussed above.

The machine control instructions including the specific inspection event sequence (i.e., how to acquire each image and how to analyze/inspect each acquired image) are generally stored as a "part program" or "workpiece program" that is specific to the particular workpiece configuration. For example, a part program defines how to acquire each image, such as how to position the camera relative to the workpiece, at what lighting level, at what magnification level, etc. Further, the part program defines how to analyze/inspect an acquired image, for example, by using one or more video tools such as edge/boundary detection video tools.

Editing a part program for a machine vision inspection system is a more complex task than editing a program for a machine tool or assembly robot or the like. For example, part programs for machine vision inspection systems include later portions that control operations and/or provide image-dependent measurement results that depend at least partially on the results determined by the execution of a previous portion of the program and/or on the particular instance of a workpiece that is being used to provide the images that are essential to the inspection operations. Furthermore, the learn mode user interface for such systems (used for part program creation and editing) may be particularly complex, requiring simultaneous display of a real-time image window, a video tool bar display, a part program representation window, a results output window (a results window, for short), an inspection feature graphical display window, a position window, a lighting window, and a measurement tool display, in order for the user to properly assess the causes and effects of their programming actions, in order to create high quality part programs. In such an editing environment, simply recognizing the location of all of the effects associated with a part program instruction may be difficult. If a user saves a partially completed part program and recalls the part program at a later time to alter or finish the programming, it may be even more difficult for them to recognize the proper association between part program instructions and their associated effects reflected in various windows. A need exists for an editing environment that can enhance user interface navigation, rapid program quality assessment, and overall part program creation and editing efficiency for machine vision inspection systems.

SUMMARY

This summary is provided to introduce a selection of concepts in a simplified form that are further described below in the Detailed Description. This summary is not intended to identify key features of the claimed subject matter, nor is it intended to be used as an aid in determining the scope of the claimed subject matter.

In order to address the considerations outlined above, it would be desirable for a machine vision inspection system to provide an editing environment including features that can enhance user interface navigation, rapid program quality assessment, and overall part program creation and editing efficiency for machine vision inspection systems by indicating the relationships between part program instructions represented in an editing window, and the related operating context and/or results displayed in other windows of the user interface. In such an editing environment, the user may more easily recognize the cause-and-effect relationships between various part program instructions in the results, and even navigate to desired parts of the user interface and/or desired specific part program instructions in the editing window by selecting a result that is of interest to them and that is displayed in a different window. This is particularly important when the part program is created and edited by recording actual control operations input by a user of the machine vision inspection system, in that the user is intuitively selecting, assessing, and/or approving the details of their control operations and/or part program instructions based on the resulting state of the machine vision inspection system and/or the measurement results associated with those control operations and/or part program instructions.

Frequently, the indication of a problem or lack of robustness in the part programming instructions will be indicated by an unexpected or "out of tolerance" result in a results window, or a misplaced measurement feature in a graphical display window, or the like, and not in the part program instructions themselves. However, it is only in the editing window that the deficient part programming instructions can be viewed such that they can be understood and reliably edited or supplemented. Furthermore, frequently, deficient part programming instructions associated with such a displayed result may not be visible in the editing window, because the editing window has a limited size in a crowded user interface, and a part program may have a very large number of instructions and/or corresponding instruction representations. Heretofore, no general purpose machine vision inspection system, and particularly no system which records actual user controlled operations in order to create a part program (e.g. as opposed to simple graphical object or text based programming systems), have provided an editing environment which reliably, robustly, and conveniently indicates the relationships between part program instruction representations in an editing window, and the related operating context and/or results displayed in other windows of a user interface, during editing operations.

In order to support this desirable editing environment, a machine vision system program editing environment including a method that provides synchronized selection and/or identification of related features in a plurality of different user interface windows is disclosed herein. In particular, one of the windows is a part program representation window, also called an editing window, where part program instruction representations are displayed for editing by a user. In one embodiment, a user may select data or another feature of interest in a window that is not the editing window (e.g., a results window, or graphical workpiece inspection feature display window) and the associated part program instruction representation is automatically displayed and/or highlighted and/or selected in the editing window such that editing commands may be conveniently implemented at the automatically highlighted or selected part program instruction representation. Conversely, in some embodiments a part program instruction representation may be selected by a user in the editing window and the associated results or feature in another window may be automatically highlighted and/or selected for evaluation.

Related editing features and functions which may be used in combination with the features disclosed herein are also described in patent applications entitled "Machine Vision System Program Editing Environment Including Real Time Context Generation Features," U.S. patent application Ser. No. 13/297,232, filed Nov. 15, 2011 (hereafter the "'232 application"); "System and Method Utilizing An Editing Initialization Block In A Part Program Editing Environment In A Machine Vision System," U.S. patent application Ser. No. 13/297,182, filed Nov. 15, 2011 (hereafter the "'182 application"); and "Machine Vision System Editing Environment For A Part Program In Which A Continuous Stream Of Image Acquisition Operations Are Performed During A Run Mode," U.S. patent application Ser. No. 13/297,220, filed Nov. 15, 2011 (hereafter the "'220 application"), each of which is hereby incorporated by reference in its entirety. The features disclosed herein are particularly useful when used in combination with the context generation features disclosed in the '232 application. This is because if a user edits an arbitrary location in a part program which is reached by the methods disclosed herein, the machine configuration or "context" at that time may be unknown, that is, it may be unknown if certain types of changes have occurred (e.g., the part being moved on the stage, etc.) relative to the machine configuration which would be expected if the part program was executed from the beginning up to that arbitrary location in the part program. Continuing edits to the part program at that "arbitrary" location without establishing the expected operating context for that location (e.g., the machine configuration, etc.) may produce unpredictable results and/or even machine damage. Due to such concerns, it has been a standard practice for some such systems to actually execute all of the instructions of a part program from the beginning up to and including any potential additional modifications or additions to the part program instructions, in order to verify that the modifications and/or additions are being programmed based on a realistic set of conditions (that is, the expected context) for their operation. However, the execution of all of the instructions of a part program to provide a realistic operating condition for modifications or additions to the instructions is impractical for large part programs (e.g., those including a large number of image acquisitions, and/or feature inspections), which are particularly common for machine vision inspection systems that provide microscopic inspection (e.g., micron resolution measurements) on macroscopic objects (e.g., objects spanning tens or hundreds of millimeters). For this reason, jumping to an arbitrary location in a part program (e.g., by the methods disclosed herein) has not been a strongly felt need, because it was not particularly useful in prior art machine vision inspection systems. However, the '232 application discloses methods for providing an editing environment which reliably and robustly provides a valid part programming editing context in near real time at an arbitrary location in a part program, during editing operations, which significantly increases the utility and time savings associated with the methods disclosed herein.

Thus, in some embodiments of the present invention, as further described below, and in the '232 application, a machine vision inspection system further comprises a run mode, a learn mode and an editing portion. The run mode is operable to execute a previously created part program using a run mode of execution. The learn mode (sometimes referred to as record mode) is operable to receive user input to control operations of the machine vision inspection system and record part program instructions corresponding to the controlled operations in order to create a part program. The learn mode also includes an editing user interface comprising the editing window which includes comprising an editable part program representation of part program instructions, wherein the part program representation comprises instruction representations. The editing portion is operable to edit a part program and includes an editing execution portion operable to execute previously recorded part program instructions according to an edit mode of execution that is different than the run mode of execution.

In various embodiments, the learn mode is configured such that it is further operable to automatically record respective surrogate data which is associated with a respective set of recorded part program instructions, wherein at least some of the surrogate data includes data which results from actual control operations corresponding to the associated set of recorded instructions. In addition, the edit mode of execution includes a surrogate execution mode. During the surrogate execution mode, for at least one set of part program instructions, if respective surrogate data has been previously recorded in association with that set of part program instructions, then at least some members of that set of part program instructions are not executed. In other words, the corresponding associated actual control operations are not executed, and the respective surrogate data is used in the subsequent operation of the surrogate execution mode as a substitute for data that would otherwise result from those actual control operations which are not executed.

In various embodiments, the learn mode may be configured to record in a respective set of recorded part program instructions an indication of whether respective surrogate data has been previously recorded in association with that respective set of part program instructions. In one embodiment, the indication is included in an initial instruction of the respective set of recorded part program instructions. In one embodiment, the respective set of recorded part program instructions may comprise instructions written in a mark up language (e.g. XML, or a derivative thereof). In various embodiments, the respective set of recorded part program instructions may comprise at least one of an element, a parent element, a container element, and a child element written in the mark up language. In at least one embodiment, the indication may comprise the presence of respective surrogate data included within that respective set of recorded part program instructions. In at least one embodiment, the indication may comprise a respective identifier included within that respective set of recorded part program instructions, the respective identifier usable to locate the corresponding respective surrogate data in a surrogate data memory portion of the machine vision inspection system.

In various embodiments, the editing portion comprises editing commands usable to edit a part program, and the editing execution portion is configured such that when the user uses the editing user interface to input an editing command to edit the program at a target location indicated in the editing window and/or the part program representation (e.g., an arbitrary part program location reached by the methods disclosed herein), then the edit mode of execution begins at a valid context starting location in the part program prior to the target location, and uses the surrogate execution mode for executing at least a portion of the part program instructions, in order to establish a valid context for editing the part program at the target location.

Additional features associated with providing and using the systems and methods disclosed herein and briefly outlined above will be understood by one of ordinary skill in the art based upon the various drawings, descriptions and claims disclosed in this application, especially when taken in conjunction with the incorporated references, wherein similarly depicted, described and/or referenced elements may be further understood by cross-referencing.

DESCRIPTION OF THE DRAWINGS

The foregoing aspects and many of the attendant advantages of this invention will become more readily appreciated as the same become better understood by reference to the following detailed description, when taken in conjunction with the accompanying drawings, wherein:

FIG. 8 is a diagram showing mark up language code instructions of the part program which correspond to some of the instruction representations of FIGS. 4-7;

FIGS. 17A and 17B are diagrams of mark up language code instructions of the part program which correspond to some of the instruction representations of FIG. 15;

DESCRIPTION

Figure 1:
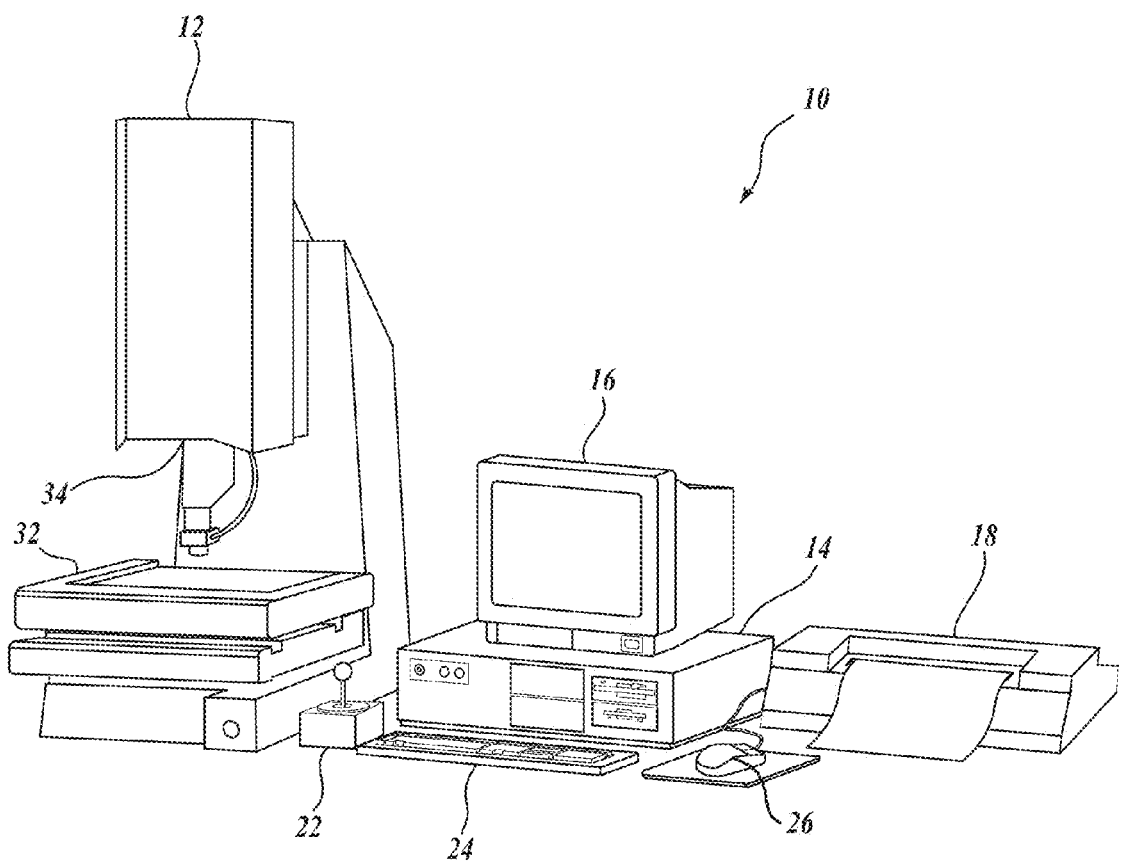
FIG. 1 is a diagram showing various typical components of a general purpose precision machine vision inspection system.

FIG. 1 is a block diagram of one example of a machine vision inspection system 10 usable in accordance with the methods described herein. The machine vision inspection system 10 includes a vision measuring machine 12 that is operably connected to exchange data and control signals with a controlling computer system 14. The controlling computer system 14 is further operably connected to exchange data and control signals with a monitor or display 16, a printer 18, a joystick 22, a keyboard 24, and a mouse 26, or the like. The monitor or display 16 may display a user interface suitable for controlling and/or programming the operations of the machine vision inspection system 10.

The vision measuring machine 12 includes a moveable workpiece stage 32 and an optical imaging system 34 which may include a zoom lens or interchangeable lenses. The zoom lens or interchangeable lenses generally provide various magnifications for the images provided by the optical imaging system 34. The machine vision inspection system 10 is generally comparable to the QUICK VISION® series of vision systems and the QVPAK® software discussed above, and similar state-of-the-art commercially available precision machine vision inspection systems. Suitable machine vision inspection system 10 are also described in commonly assigned U.S. Pat. Nos. 7,454,053; 7,324,682; 8,111,938; and 8,111,905, which are each incorporated herein by reference in their entireties.

Figure 2:
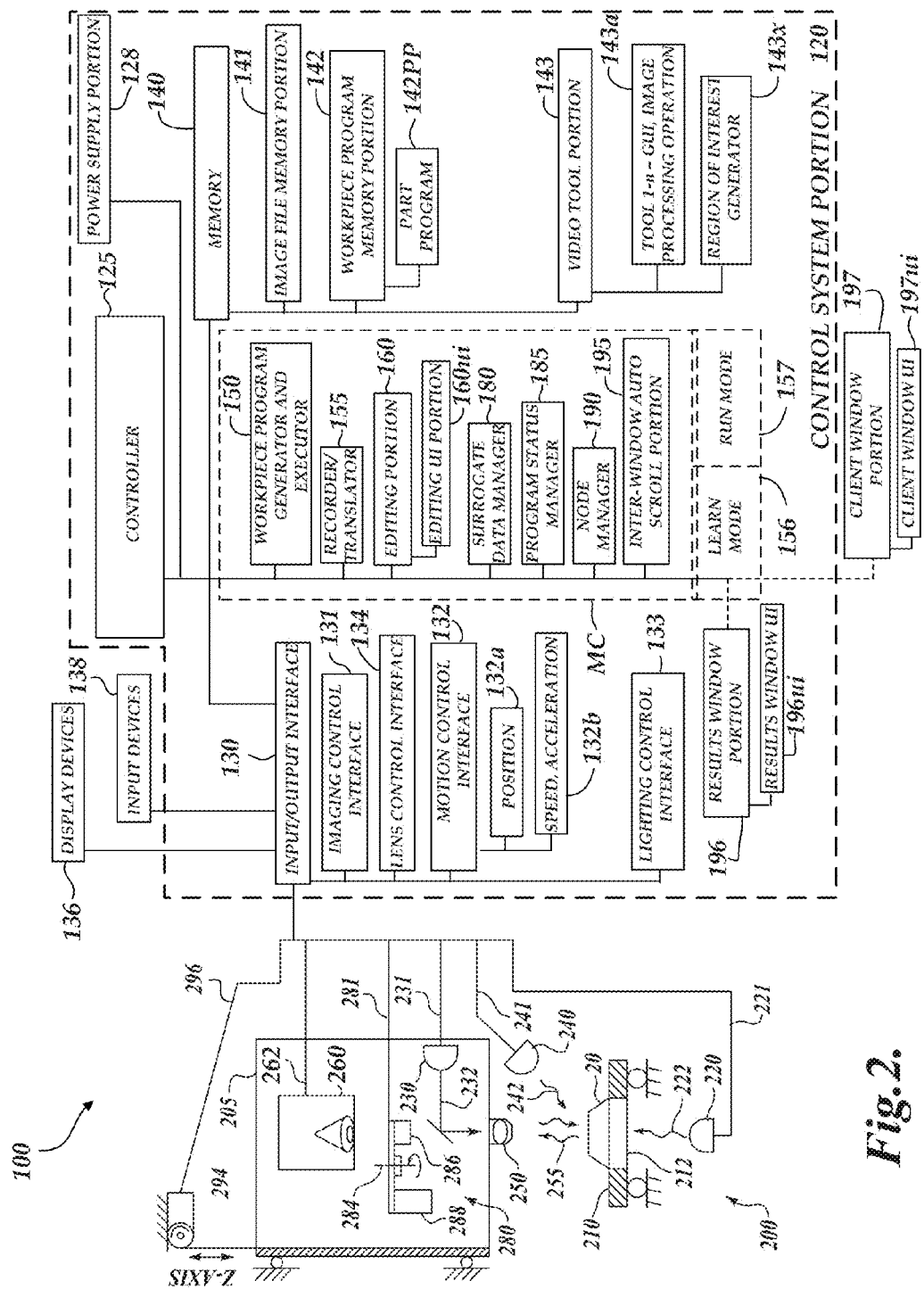
FIG. 2 is a block diagram of a control system portion and a vision components portion of a machine vision inspection system similar to that of FIG. 1, and including features usable in various embodiments according to this invention.

FIG. 2 is a block diagram of a control system portion 120 and a vision components portion 200 of a machine vision inspection system 100 similar to the machine vision inspection system of FIG. 1, and includes features usable in various embodiments according to the present invention. As will be described in more detail below, the control system portion 120 is utilized to control the vision components portion 200. As shown in FIG. 2, the vision components portion 200 includes an optical assembly portion 205, light sources 220, 230, and 240, and a workpiece stage 210 having a central transparent portion 212. The workpiece stage 210 is controllably movable along X and Y axes that lie in a plane that is generally parallel to the surface of the stage where a workpiece 20 may be positioned. The optical assembly portion 205 includes a camera system 260, an interchangeable objective lens 250, and may include a turret lens assembly 280 having lenses 286 and 288. Alternatively to the turret lens assembly, a fixed or manually interchangeable magnification-altering lens, or a zoom lens configuration, or the like, may be included. The optical assembly portion 205 is controllably movable along a Z-axis that is generally orthogonal to the X and Y axes, by using a controllable motor 294, as described further below.

A workpiece 20, or a tray or fixture holding a plurality of workpieces 20, which is to be imaged using the machine vision inspection system 100 is placed on the workpiece stage 210. The workpiece stage 210 may be controlled to move relative to the optical assembly portion 205, such that the interchangeable objective lens 250 moves between locations on a workpiece 20, and/or among a plurality of workpieces 20. One or more of a stage light 220, a coaxial light 230, and a surface light 240 may emit source light 222, 232, or 242, respectively, to illuminate the workpiece or workpieces 20. The source light is reflected or transmitted as workpiece light 255, which passes through the interchangeable objective lens 250 and the turret lens assembly 280 and is gathered by the camera system 260. The image of the workpiece(s) 20, captured by the camera system 260, is output on a signal line 262 to the control system portion 120. The light sources 220, 230, and 240 may be connected to the control system portion 120 through signal lines or busses 221, 231, and 241, respectively. To alter the image magnification, the control system portion 120 may rotate the turret lens assembly 280 along axis 284 to select a turret lens, through a signal line or bus 281.

In various exemplary embodiments, the optical assembly portion 205 is movable in the vertical Z-axis direction relative to the workpiece stage 210 using a controllable motor 294 that drives an actuator, a connecting cable, or the like, to move the optical assembly portion 205 along the Z-axis to change the focus of the image of the workpiece 20 captured by the camera system 260. The term Z-axis, as used herein, refers to the axis that is intended to be used for focusing the image obtained by the optical assembly portion 205. The controllable motor 294, when used, is connected to the input/output interface 130 via a signal line 296.

As shown in FIG. 2, in various exemplary embodiments, the control system portion 120 includes a controller 125, a power supply portion 128, the input/output interface 130, a memory 140, a workpiece program generator and executor 150, a recorder/translator 155, and a learn mode portion 156, a run mode portion 157, and editing portion 160, a surrogate data manager 180, a program status manager 185, a node manager 190, an inter-window auto-scroll portion 195, and a results window portion 196. Each of these components, as well as the additional components described below, may be interconnected by one or more data/control buses and/or application programming interfaces, or by direct connections between the various elements.

The input/output interface 130 includes an imaging control interface 131, a motion control interface 132, a lighting control interface 133, and a lens control interface 134. The motion control interface 132 may include a position control element 132a and a speed/acceleration control element 132b, although such elements may be merged and/or indistinguishable. The lighting control interface 133 controls, for example, the selection, power, on/off switch, and strobe pulse timing if applicable, for the various corresponding light sources of the machine vision inspection system 100.

The memory 140 includes an image file memory portion 141, a workpiece program memory portion 142 that may include one or more part programs 142PP or the like, and a video tool portion 143. The video tool portion 143 includes video tool portion 143a and other video tool portions, which determine the GUI, image processing operation, etc., for each of the corresponding video tools. Many known video tools are included in commercially available machine vision inspection systems, such as the QUICK VISION® series of vision systems and the associated QVPAK® software, discussed above. The video tool portion 143 also includes a region of interest (ROI) generator 143x that supports automatic, semi-automatic and/or manual operations that define various ROIs that are operable in various video tools included in the video tool portion 143.

In general, the memory portion 140 stores data usable to operate the vision system components portion 200 to capture or acquire an image of the workpiece 20 such that the acquired image of the workpiece 20 has desired image characteristics. The memory portion 140 may also store inspection result data, may further store data usable to operate the machine vision inspection system 100 to perform various inspection and measurement operations on the acquired images (e.g., implemented, in part, as video tools), either manually or automatically, and to output the results through the input/output interface 130. The memory portion 140 may also contain data defining a user interface operable through the input/output interface 130. As will be described in more detail below with reference to FIGS. 14-19, in one embodiment, when editing a part program, rather than being required to execute all of the steps of the part program in order to generate the needed context for continuing edits, certain context can be simulated using previously saved data as surrogate data. The memory portion 140 may also store such surrogate data.

The signal lines or busses 221, 231, and 241 of the stage light 220, the coaxial light 230, and the surface light 240, respectively, are all connected to the input/output interface 130. The signal line 262 from the camera system 260 and the signal line 296 from the controllable motor 294 are connected to the input/output interface 130. In addition to carrying image data, the signal line 262 may carry a signal from the controller 125 that initiates image acquisition.

One or more display devices 136 (e.g., the display 16 of FIG. 1) and one or more input devices 138 (e.g., the joystick 22, keyboard 24, and mouse 26 of FIG. 1) can also be connected to the input/output interface 130. The display devices 136 and input devices 138 can be used to display a user interface, which may include various user interface features that are usable to perform inspection operations, and/or to create and/or modify part programs, to view the images captured by the camera system 260, and/or to directly control the vision system components portion 200. In particular, according to various exemplary embodiments of the present invention, the display devices 136 and input devices 138 are used to present various user interface features usable to allow rapid, efficient, intuitive, and flexible editing of part programs on the machine vision inspection system 100.

The workpiece program generator and executor 150, recorder/translator 155, learn mode portion 156, run mode portion 157, editing portion 160, surrogate data manager 180, program status manager 185, node manager 190, and an inter-window auto scroll portion 195 may in one embodiment all be considered to be part of a general machine controller block MC that is linked to the controller 125. Additionally, a client window portion 197 may be linked to the controller 125. A client window may be considered to be outside of, but communicating to inter-operate with, the control system portion 120 in some embodiments. The workpiece program generator and executor 150 is responsible for creating and executing part programs. It will be appreciated that the terms "workpiece program" and "part program" may be used interchangeably herein.

In accordance with the operations of the workpiece program generator and executor 150, in various exemplary embodiments, when a user utilizes the machine vision inspection system 100 to create a part program for the workpiece 20, the user generates part program instructions either by explicitly coding the instructions automatically, semi-automatically, or manually, using a workpiece programming language, and/or by generating the instructions by operating the machine vision inspection system 100 in a learn mode (e.g., as controlled by the learn mode portion 156) to provide a desired image acquisition training sequence. For example, a training sequence may comprise positioning a workpiece feature in the field of view (FOV), setting light levels, focusing or autofocusing, acquiring an image, and providing an inspection training sequence applied to the image (e.g., using video tools). The learn mode operates such that the sequence(s) are captured or recorded and converted to corresponding part program steps (i.e., instructions). These part program steps, when the part program is executed in a run mode (e.g., as controlled by the run mode portion 157), will cause the machine vision inspection system to reproduce the trained image acquisition and inspection operations to automatically inspect a workpiece or workpieces matching the workpiece used when creating the part program.

The recorder/translator 155 is utilized for translating machine operations into part program code. In other words, if a user performs an action (e.g., such as altering a video tool that is used to measure a feature on a workpiece) an instruction is generated that is translated into a machine readable language, and a reverse translation may also be performed. As will be described in more detail below, in certain embodiments disclosed herein, certain instructions in a part program may also be translated into instruction representations in a user interface. In some embodiments, the part program instructions may be written in a mark up type language code. In one specific example embodiment, the mark up language code may be MIML code. The editing portion 160 provides or activates various operations and user interface features related to editing a part program within an editing user interface portion 160*ui*, which may include a part program representation window as described in greater detail below.

The surrogate data manager 180 need not be present to practice all embodiments of the present invention. However, the surrogate data manager 180 may be used in combination with the present invention in some embodiments. Briefly, the surrogate data manager 180 links to surrogate data, which in accordance with the present invention, may be recorded in a part program. In certain implementations, the surrogate data manager 180 is responsible for obtaining the surrogate data from an output where it would normally be generated, and providing the surrogate data to be written into the part program. The surrogate data manager 180 is described in greater detail below.

The program status manager 185, in one embodiment, manages whether programs are protected or unprotected. In one implementation, an unprotected part program may include stored surrogate data, while a protected part program has had any surrogate data removed. In one example embodiment, protected programs are programs for which the editing process has been completed, such as may be utilized in a factory in a run mode. In one embodiment, a user may select a part program that is to be protected, at which point the program status manager 185 automatically removes all of the surrogate data so that the part program is not burdened with extra execution steps at run time. The program status manager 185 is also responsible for when a program is unprotected, such that the surrogate data remains recorded in the part program and when a part program is recalled by the editing portion 160, the surrogate data is indicated as being available.

In one embodiment, the node manager 190 is responsible for managing node numbers that are assigned to nodes in a part program. In one implementation, within a representation of a part program, each of the instruction representations is assigned a node number. In certain implementations, an organizational tree structure may be utilized wherein there are parent nodes and child nodes. In certain implementations, every line of a part program representation that is generated by the recorder/translator 155 is assigned a node number, or a guaranteed unique identifier, of the like by the node manager 190. As described in greater detail below, in some embodiments the inter-window auto scroll portion 195 may utilize the node numbers assigned by the node manager 190 to display related elements of associated part program elements and corresponding editing functions in different windows at the same time. In other words, if a user wishes to see which measurements of a workpiece are related to which instruction representations and coded instructions in a part program, the inter-window auto scroll portion 195 will automatically scroll in the respective windows to the relevant lines in the part program representation and/or coded instructions that correspond to the relevant node number.

The results window portion 196 provides or activates various operations and user interface features related to editing a part program including displaying results of measurements performed by machine vision system inspection operations within a results window user interface 196*ui*. However, more generally, the results window portion 196 and/or results window user interface 196*ui* may comprise the various features and attributes described elsewhere in this disclosure, as well as extensions and are alternatives which will be apparent to one of ordinary skill in the art based on inter-window auto scroll portion features or attributes depicted, described and/or referenced in this disclosure.

Figure 3:
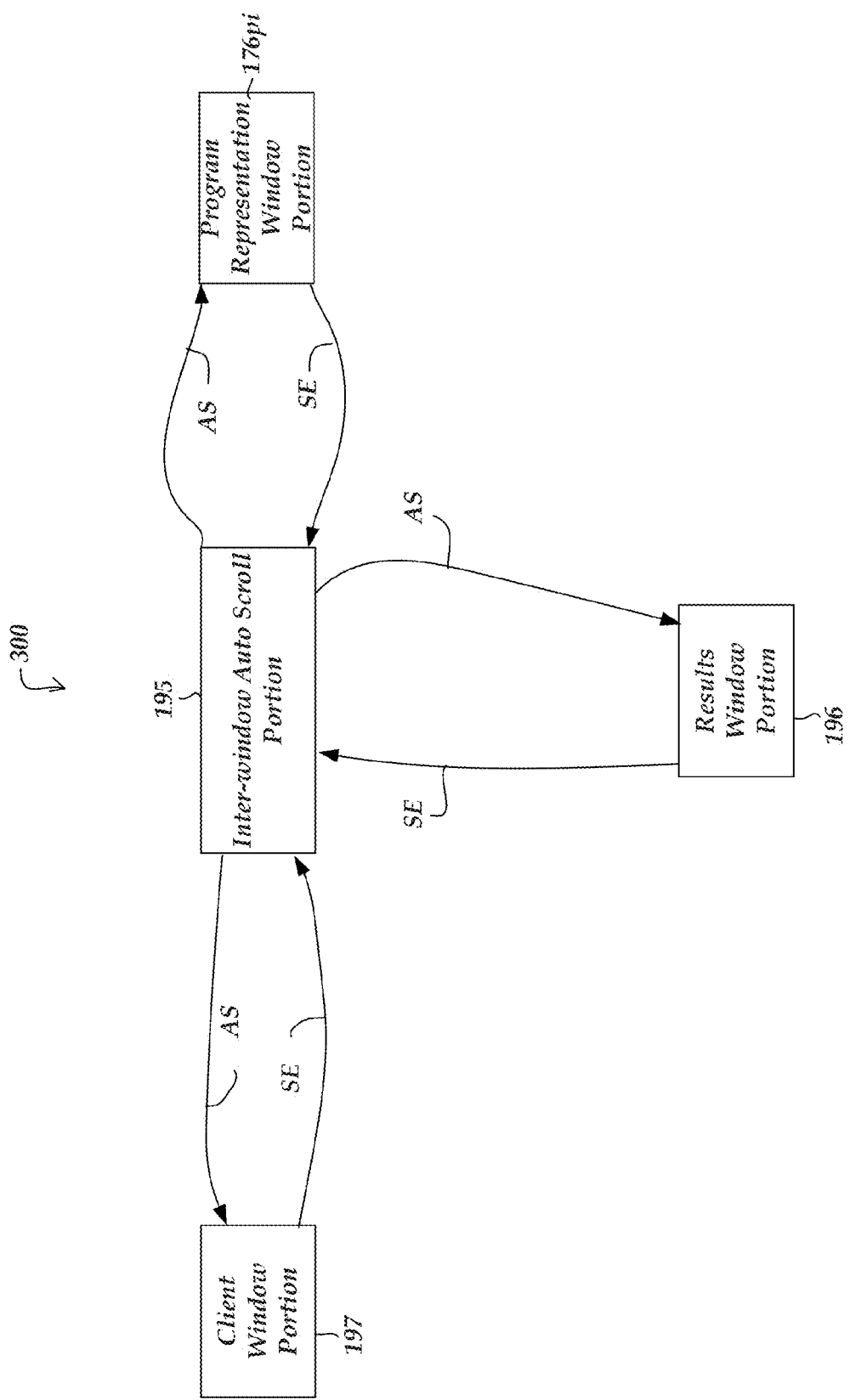
FIG. 3 is a functional schematic representation of communication routines and/or operations that may be used to implement inter-window auto scroll operations as disclosed herein.

The client window portion 197 provides or activates various operations and user interface features related to editing a part program including displaying features related to measurements performed by machine vision system inspection operations within a client window user interface 197*ui*. However, more generally the client window portion 197 and/or client window user interface 197*ui* may comprise the various features and attributes described elsewhere in this disclosure, as well as extensions and/or alternatives which will be apparent to one of ordinary skill in the art based on inter-window auto scroll portion features or attributes depicted, described and/or referenced in this disclosure. A client window need not be present in some embodiments of the present invention. A client window may be associated with a program or routine which is not essential to the basic operation of the machine vision inspection system, but which may provide enhanced functionality or ease of use. The graphic view window portion represented by the graphic view window shown in FIGS. 4-7 is one example of a client window portion 197. As shown in FIG. 3, a client window may have inter-window auto scroll user interface features and attributes that are substantially similar to those disclosed herein for a results window.

Further regarding FIG. 2, many features of FIG. 2 may be understood based on the descriptions of their analogous or substantially similar counterparts which are similarly depicted, described and/or referenced elements in the co-pending applications previously incorporated herein by reference. The editing portion 160 and/or the editing UI portion 160*ui*, described in greater detail below, may have numerous features similar or identical to analogous features described in the incorporated references. The inter-window auto scroll portion 195 may comprise the various features and attributes disclosed herein, as well as extensions and alternatives which will be apparent to one of ordinary skill in the art based on inter-window auto scroll portion features or attributes depicted, described and/or referenced in this disclosure. In addition, the inter-window auto scroll portion 195 may alternatively be referred to as an auto scroll manager, and may have some features similar to features described in relation to the auto scroll manager described in the incorporated references.

It will be understood that the editing portion 160, the inter-window auto scroll portion 195, the node manager 190, and in some embodiments, the surrogate data manager 180, cooperate with one another to provide the various features disclosed herein for enhancing the part program editing environment of a machine vision inspection system. In some embodiments, these various portions may alternatively be configured such that they are part of one another, or otherwise combined and/or indistinguishable. Thus, it will be appreciated that the configuration of these portions shown in FIG. 2 is exemplary only, and not limiting.

FIG. 3 is a functional schematic representation 300 of one embodiment of communication routines and/or operations that may be implemented by an inter-window auto scroll portion 195 (e.g., the inter-window auto scroll portion 195 shown in FIG. 2) to provide inter-window auto scroll features disclosed herein. FIG. 3 schematically shows the inter-window auto scroll portion 195, a program representation window portion 176*pi*, a results window portion 196, and a client window portion 197. It should be understood that a "window portion" may include a displayed user interface window, as well as its associated features and the underlying routines which provide its operations. A window portion may also be referred to simply as a window herein. The program representation window portion 176*pi* may also sometimes be referred to as a program instruction representation window, or an editing window, here and/or in the incorporated references.

In the embodiment shown in FIG. 3, the inter-window auto scroll portion 195 interacts with the program representation window portion 176*pi* through a program representation window selection event notification SE and a program representation window auto scroll notification AS. The inter-window auto scroll portion 195 interacts with the client window portion 197 through a result window selection event notification SE and a result window auto scroll notification AS. The inter-window auto scroll portion 195 interacts with the client window portion 197 through a client window selection event notification SE and a client window auto scroll notification AS. The various selection event notifications SE are triggered independently. That is, any window that is the host of selection of an element that is of a type that may have an associated element in another window may issue a selection event notification SE in response to that selection, based on a routine or operations of that window that are triggered by the selection event.

For example, a selection event may be the user selecting an instruction representation in the program representation window, or selecting a result in the result window, or selecting a graphical element in a client window. Selection may be accomplished by using a user interface input device and a known element selection method such as a mouse click on the element in a user interface, or the like. In contrast, in various embodiments, the auto scroll notifications AS to each applicable window are triggered in response to any selection event notification, and are generally sent to all applicable windows (however, it is not necessary to send an auto scroll notification to the window that created the current selection event notification).

The auto scroll notifications AS are based on a routine or operations of the Inter Auto Scroll Portion that are triggered by a selection event notification SE. In response to receiving an auto scroll notification AS, a window displays and/or highlights a feature or element in that window that is associated with the particular element that was selected in the window that issued the triggering selection event notification SE, as described in greater detail below. One aspect of the novelty of the systems and methods disclosed herein lies in the combination of various attributes and features disclosed herein in relation to providing a machine vision system part programming and editing environment. Such a combination has not been previously contemplated or achieved in relation to the particular operating and programming complexity of a machine vision inspection system, in order to provide the related part programming user interface features disclosed herein.

In one embodiment, FIG. 3 may be implemented using known "publisher-subscriber" methods, which are sometimes implemented using XML like languages (e.g., as used for notifications between web pages). In various embodiments, a publisher-subscriber method may be implemented by adapting methods such as a list-based method, or a broadcast-based method, or a content-based method to support the features disclosed herein. In a machine vision inspection system, the publishers and subscribers are generally located in the same processing space, and it is possible for the identity of the "subscriber" windows to be known by the "publisher." Applicable to such cases, U.S. Pat. No. 8,028,085 ("the '085 patent"), which is hereby incorporated herein by reference in its entirety, describes low latency methods which may be adapted to support the features disclosed herein.

In various embodiments, associated or corresponding features in the various windows may be established as part program instructions are created and/or recorded during learn mode. For example, in one embodiment, each of the corresponding features may be assigned or labeled with the same "identifier" in each window portion as a means of establishing and recording their association. In such an embodiment, the selection event notification SE may include the identifier of the selected element, which may be passed through the auto scroll notification AS such that the receiving window may auto scroll (e.g., display and/or highlight) the associated feature or element based on that identifier, as described in greater detail below.

Figure 4:
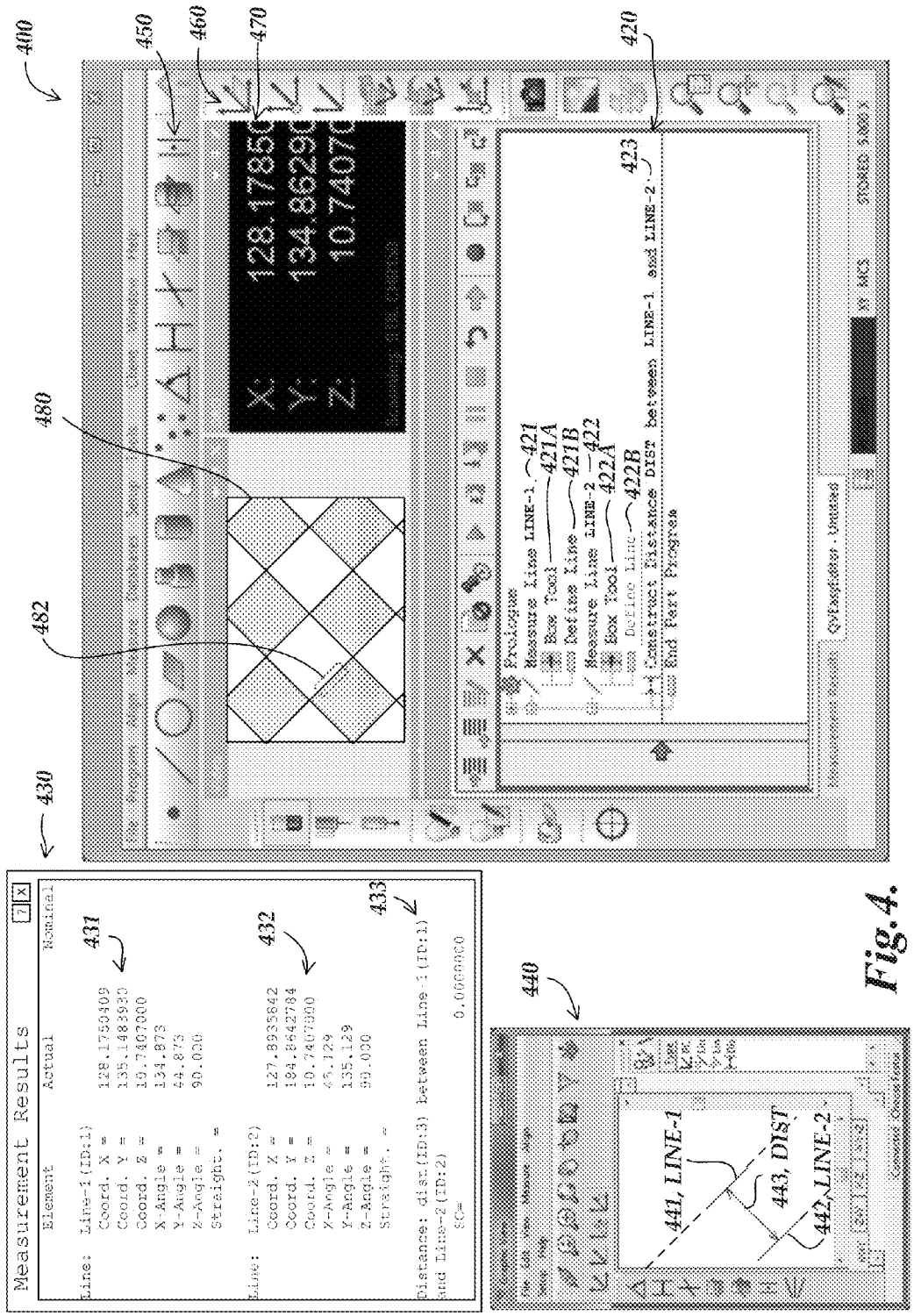
FIG. 4 is a diagram of a user interface including an editing user interface and a results window.

FIG. 4 is a diagram of a learn mode user interface 400 comprising one embodiment of an editing environment including a plurality of windows that can be configured and operated according the principles disclosed herein. The editing environment includes part program instruction representations (e.g., such as "measure line" named "LINE-1" using a "box tool") depicted in a part program representation window 420 (which may be used as, and referred to as, an editing window 420 in various embodiments), measurement results from those part program instructions (e.g., measurement result coordinate X=128.1750409) depicted in a results window 430, and representations of various related measured features (e.g., including line features 441 and line 442, and a distance 443 between the lines indicated by double headed arrow) depicted superimposed on a CAD model in a graphic view client window 440. This user interface 400 has counterpart elements described in the incorporated references, and its various embodiments may be further understood based description in those references. Generally speaking, the features or elements generated in the windows 430 and 400 are generated by the learn mode execution of recorded part program instructions corresponding to the instruction representations depicted in the part program representation window 420. In the state shown in FIG. 4, none of the elements have been selected by a user.

The user interface 400 also includes a toolbar 450, a toolbar 460, a stage position display 470 and a field of view display 480. The toolbar 450 comprises various user tools (e.g., measurement video tools) arranged horizontally in the upper portion of the user interface 400. The toolbar 460 comprises user tools (e.g., alignment and magnification tools) arranged vertically on the right hand portion of the user interface. The stage position display 470 displays X, Y, and Z coordinates indicating a position of the stage 32. The field of view display 480 displays a field of view of the machine vision inspection system 100 as imaged by the camera 260, and for reference, schematically displays in dashed outline the location where a box tool region of interest corresponding to the box tool instruction representation 422A would appear as it is defined and recorded by a user.

The part program instruction representations depicted in the part program representation window 420 include parent node instruction representations 421, 422, and 423. The parent node instruction representation 421 includes children node instruction representations 421A and 421B. The parent node instruction representation 421 indicates that a box tool will be opened for measuring the line feature 441, represented as LINE-1, wherein the instruction representation 421A indicates that the user utilizes the box tool to determine edge points of LINE-1 which are then utilized as indicated by the instruction representation 421B to define LINE-1. The parent node instruction representation 422 includes children node instruction representations 422A and 422B. The parent node instruction representation 422 indicates that a box tool will be opened for measuring the line feature 442, represented as LINE-2, wherein the instruction representation 422A indicates that the user utilizes the box tool to determine edge points of LINE-2 which are then utilized as indicated by the instruction representation 422B to define LINE-2. The instruction representation 423 indicates that a distance 443, represented as "DIST," is determined between LINE-1 and LINE-2. The results window 430 displays measurement results 431, 432, and 433 which correspond to the instruction representations 421, 422, and 423, respectively.

Figure 5:
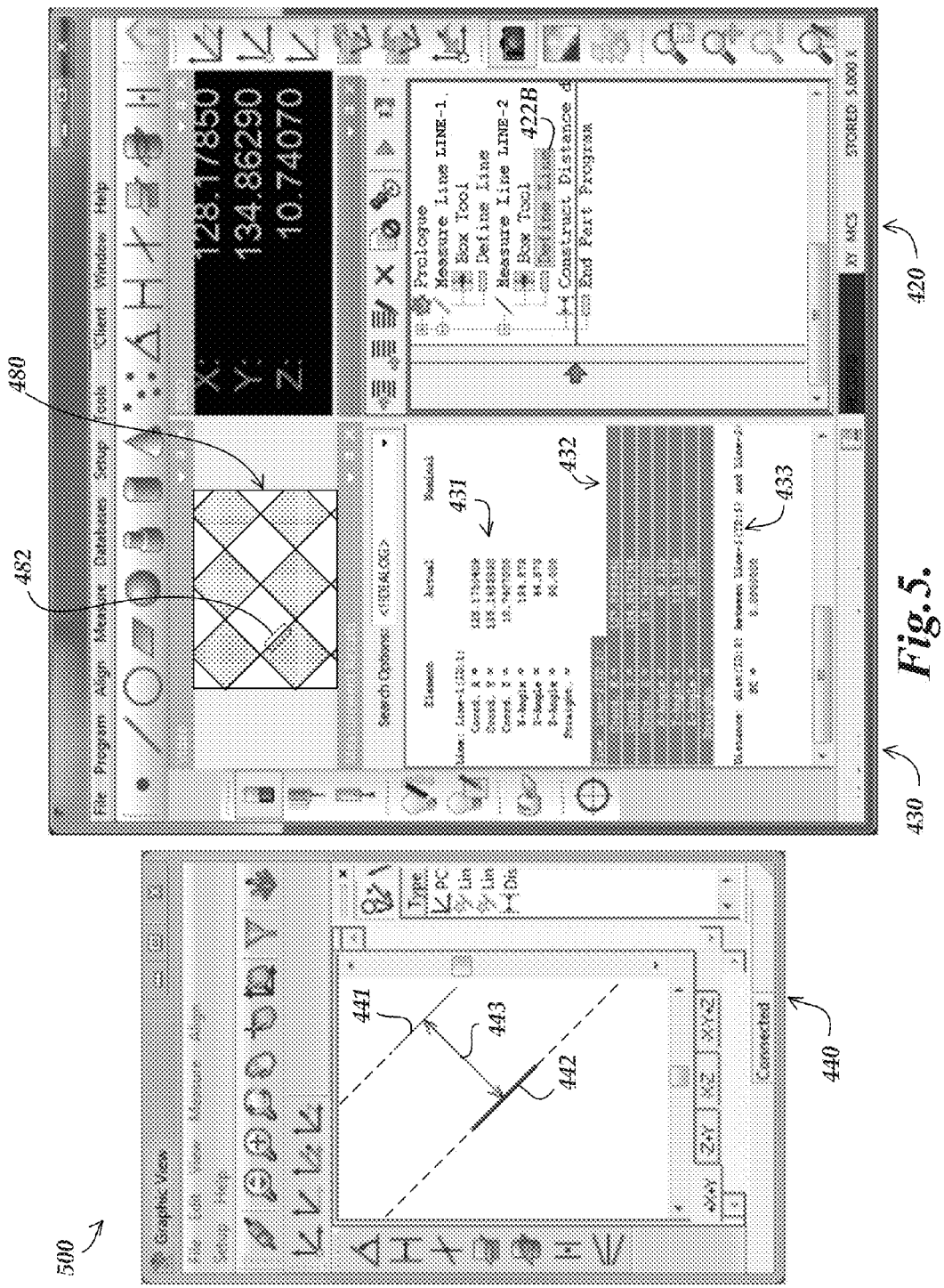
FIG. 5 is a diagram illustrating operations of the user interface of FIG. 4.

FIG. 5 is a diagram illustrating operations of the user interface of FIG. 4 according to one aspect of one embodiment according to the principles disclosed herein. Briefly, the part program instruction representation 422B is highlighted in the part program representation window 420, and the related line measurement result LINE-2 is highlighted in the results window 430, and a related line feature 441 is highlighted in the client window 440. In various embodiments, when the user selects any one of these elements in one of the windows, the other corresponding elements are advantageously highlighted or otherwise marked in the other windows (e.g., as illustrated).

The method(s) depicted and described with reference to FIG. 3 may be used to provide the necessary notifications between windows, and each window may include routines or operations that provide the corresponding highlighting and/or marking. This provides the benefits outlined above. In one embodiment, a selection of an element in the results window 430 or the client window 440 results in a transfer of control to the part program representation window, and/or selection of the corresponding part program instruction representation in that window, once it receives the associated selection event notification (e.g., as described with reference to FIG. 3), such that editing operations are immediately facilitated.

Figure 6:
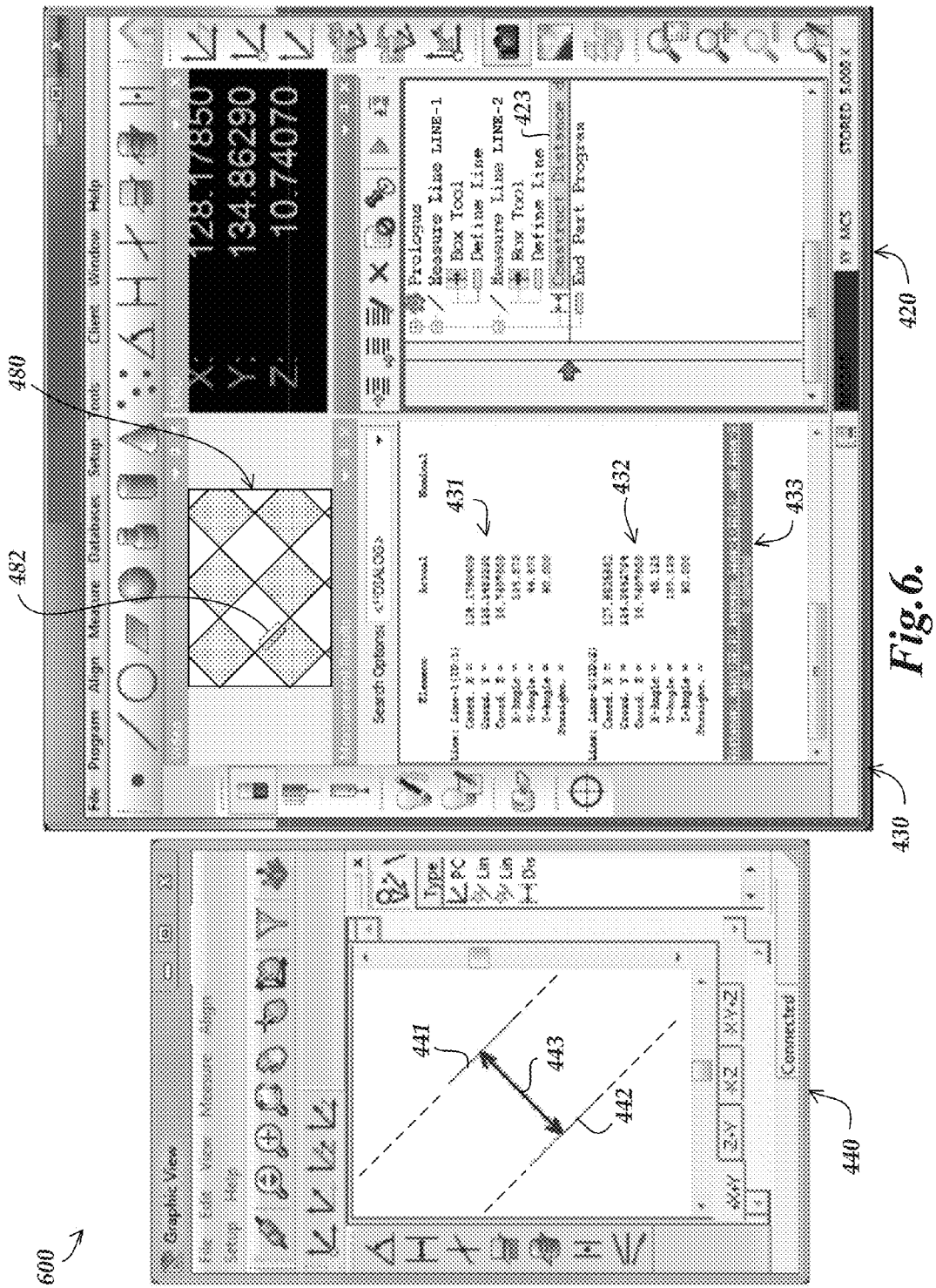
FIG. 6 is a diagram illustrating operations of the user interface of FIG. 4.

FIG. 6 is a second diagram illustrating operations of the user interface of FIG. 4 according to another aspect of one embodiment according to the principles disclosed herein. FIG. 6 shows a similar example of the relationship between corresponding elements in the various windows. Briefly, the part program instruction representation 423 (a distance measurement between lines) is selected, and therefore highlighted in the part program representation window 420, and the related distance measurement result DIST is highlighted in the results window 430, and the related distance 443 is highlighted in the client window 440. In some embodiments, execution of a part program instruction representation 423 (e.g., to train a video tool or confirm an operation result, or the like) may leave the corresponding instruction in a "selected" state, insofar as it may be highlighted, along with the corresponding elements in other applicable windows.

Figure 7:
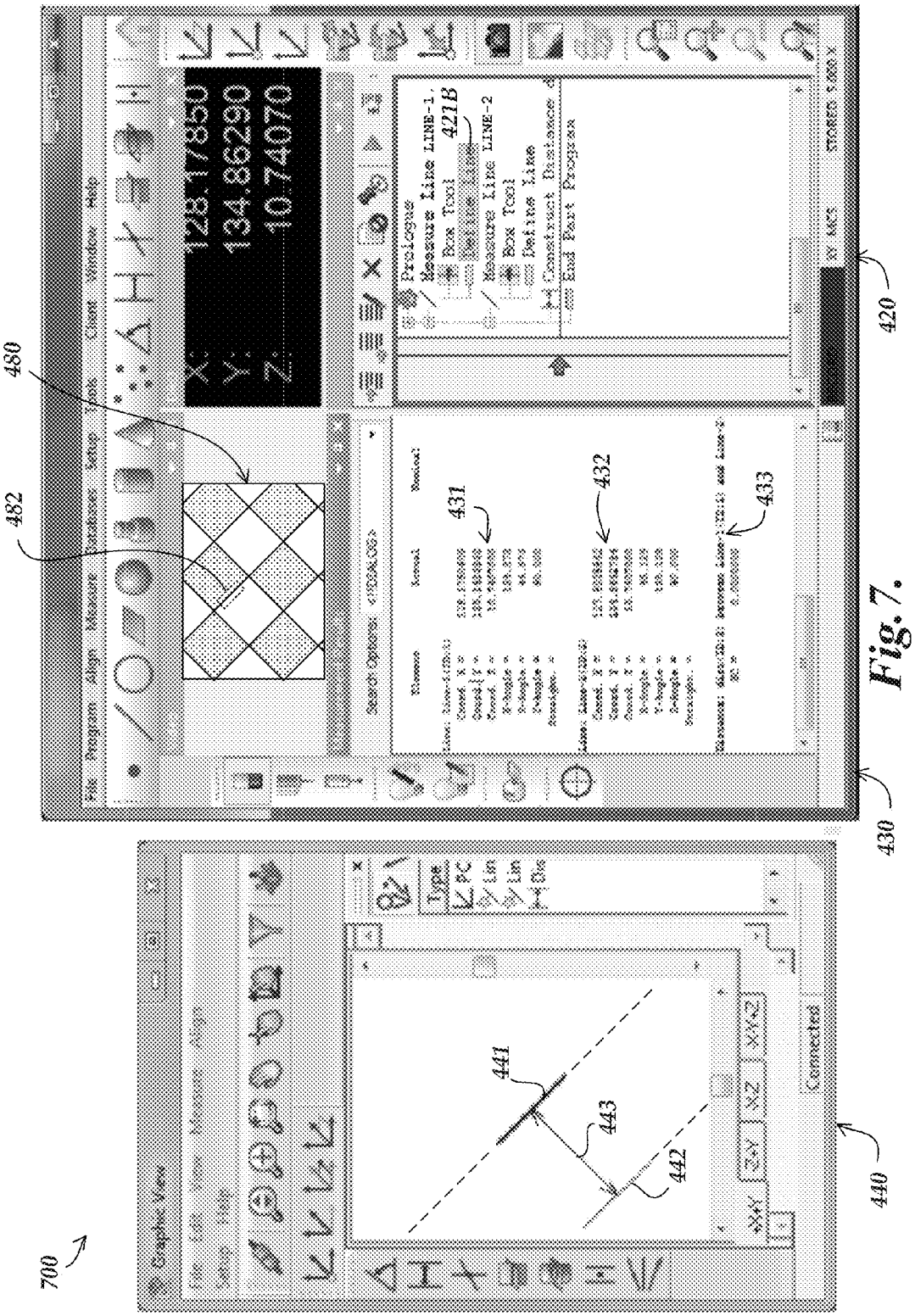
FIG. 7 is a diagram illustrating operations of the user interface of FIG. 4.

FIG. 7 is a third diagram illustrating operations of the user interface of FIG. 4 according to another aspect of one embodiment according to the principles disclosed herein. FIG. 7 shows an example wherein the selection of a feature in the client window 440 results in marking the corresponding element in the part program representation window 420 (that is, the editing window), but in contrast to previously described embodiments, does not affect the results window 430. Of course, in some embodiments, selection of an element in the results window 430 may have an analogous behavior, that is, the editing window 420 may be affected, but the client window 440 may be unaffected, if desired). Such an embodiment that does not affect all windows simultaneously may have advantages for some particular window types or programming situations. More specifically, in the embodiment shown in FIG. 7, the part program instruction representation 421B is highlighted in the part program representation window 420 when the related line measurement result LINE-1 is selected (and highlighted, in some embodiments) in the results window 430, but the related distance 443 is not highlighted in the client window 440 at that time.

It should be appreciated that with regard to FIGS. 5-7, any window may include elements that are "out of view" at the time of a selection event notification (e.g., in the case of a large part program, or workpiece CAD image, or the like). The user may scroll the contents of any window individually, prior to selection, and the contents of other windows need not be adjusted at that time. Then, in various embodiments, upon a selection event notification if the corresponding element in any window is not currently in the display area, a routine or operations of that window will automatically cause its contents to jump or scroll to the element corresponding to the selection event notification. That is, if an element in one window related to a user-selected element in another window is not visible in its respective window, then the learn mode user interface may be configured to automatically "scroll" the display in its respective window until the element related to the user-selected element is visible its respective window. It should also be appreciated that although the word "scroll" or "auto scroll" may be used herein, these words are used for convenience only, and are not limiting. More generally, the element corresponding to the selected element may be made visible in its respective window, by any convenient and/or known method, including simply regenerating the window with the desired contents, or the like.

FIG. 8 is a diagram 800 including mark up language code instructions of a part program, which may correspond to some of the instruction representations of FIGS. 4-7. In particular, FIG. 8 depicts an implementation of an automatically defined identifier which may be used in some embodiments to implement user interface synchronizing "auto scroll" features outlined above, and further below in relation to some or all of FIGS. 9-13. In particular, FIG. 8 shows a particular implementation comprising an XML-like code language wherein a "node ID" value 805 or identifier 805 corresponding to the measurement of LINE-2 is automatically generated and inserted into a part program instruction, when the part program instruction is recorded.

As shown in FIG. 8, a point associated with an end of LINE-2 is illustrated as part of data 810. In one embodiment, a node ID may be used by the inter-window auto scroll portion to be assigned to associated part program instructions and their corresponding instructions representations displayed in the part program representation window and/or the results generated results window and/or a client window based on the execution of those instructions. Thus, related features in various windows become associated in the inter-window auto scroll portion.

Alternatively, the results window and/or the client window and/or the part program representation window (that is, the editing window) may generate their own element identifiers at the time that they generate their displayed elements, and pass this information to the inter-window auto scroll portion, which may form an association between the various identifiers in a stored identifier association table, or the like. It should be appreciated that in some embodiments, the part program instructions in the part program instruction representations may be handled within a single application or subroutine of the machine vision inspection system control software, such that a part program instruction or its corresponding part program instruction representation may be represented by a single identifier which is usable by the inter-window auto scroll portion in relation to either of these elements.

FIGS. 9-13 are briefly described below. Various features and attributes associated with various implementations of FIGS. 9-13 may be realized by interpreting FIGS. 9-13 in light of the various figures and disclosure included herein, as well as consideration of the description and disclosure included in the incorporated references.

Figure 9:
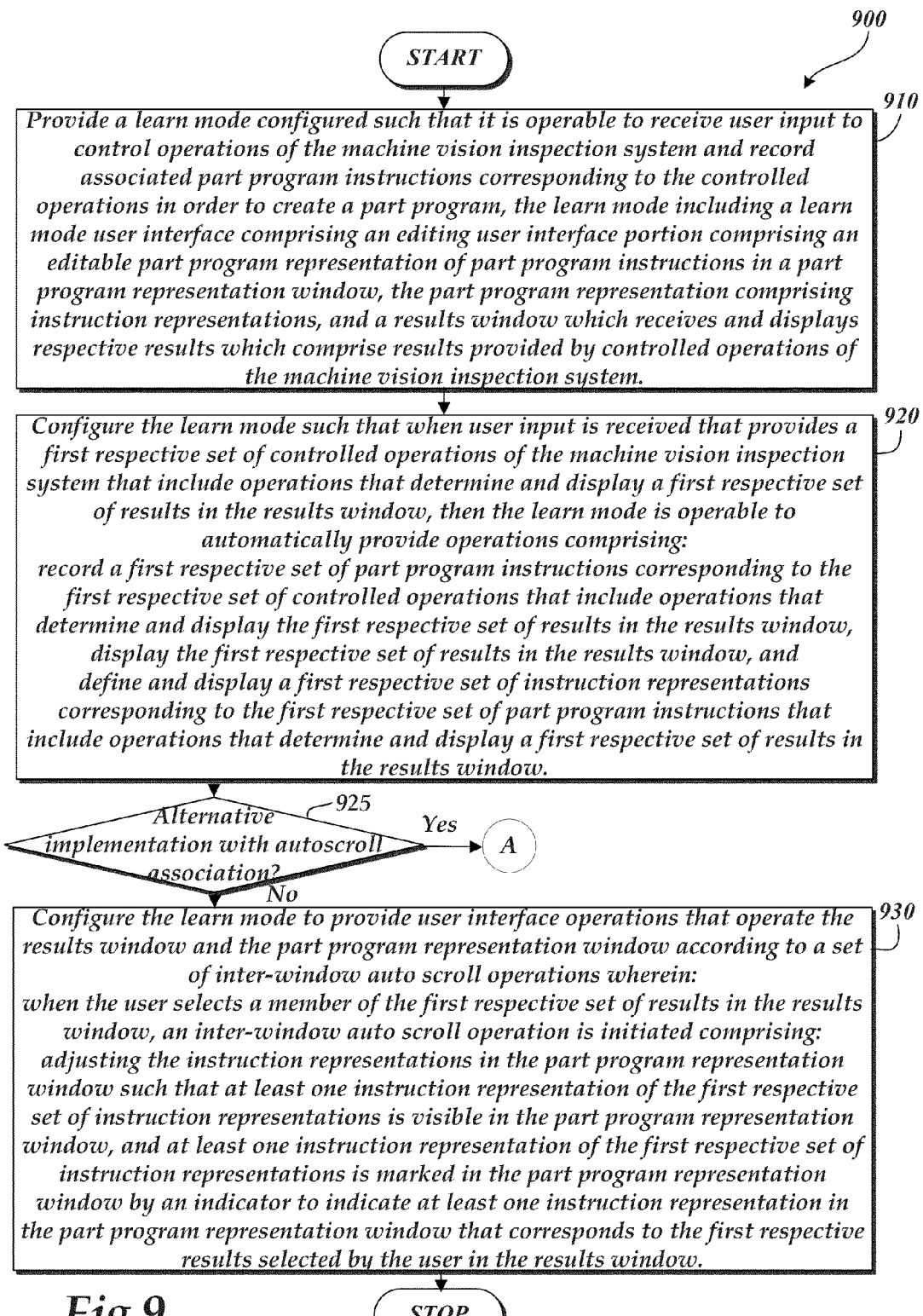
FIG. 9 is a flow diagram illustrating one embodiment of a routine for providing a machine vision system program editing environment.

FIG. 9 is a block diagram illustrating one embodiment of a routine 900 for providing a machine vision system program editing environment operated according to principles outlined above and further below.

As shown in FIG. 9, at a block 910, a machine vision inspection system learn mode is provided which is configured such that it is operable to receive user input to control operations of the machine vision inspection system and record associated part program instructions corresponding to the controlled operations in order to create a part program, the learn mode including a learn mode user interface comprising an editing user interface portion comprising an editable part program representation of part program instructions in an editing window, the part program representation comprising instruction representations, and a results window which receives and displays respective results which comprise results provided by controlled operations of the machine vision inspection system.

At a block 920, the learn mode is configured such that when user input is received that provides a first respective set of controlled operations of the machine vision inspection system that include operations that determine and display a first respective set of results in the results window, then the learn mode is operable to automatically provide operations comprising:

record a first respective set of part program instructions corresponding to the first respective set of controlled operations that include operations that determine and display the first respective set of results in the results window, display the first respective set of results in the results window, and define and display a first respective set of instruction representations corresponding to the first respective set of part program instructions that include operations that determine and display a first respective set of results in the results window.

Figure 10:
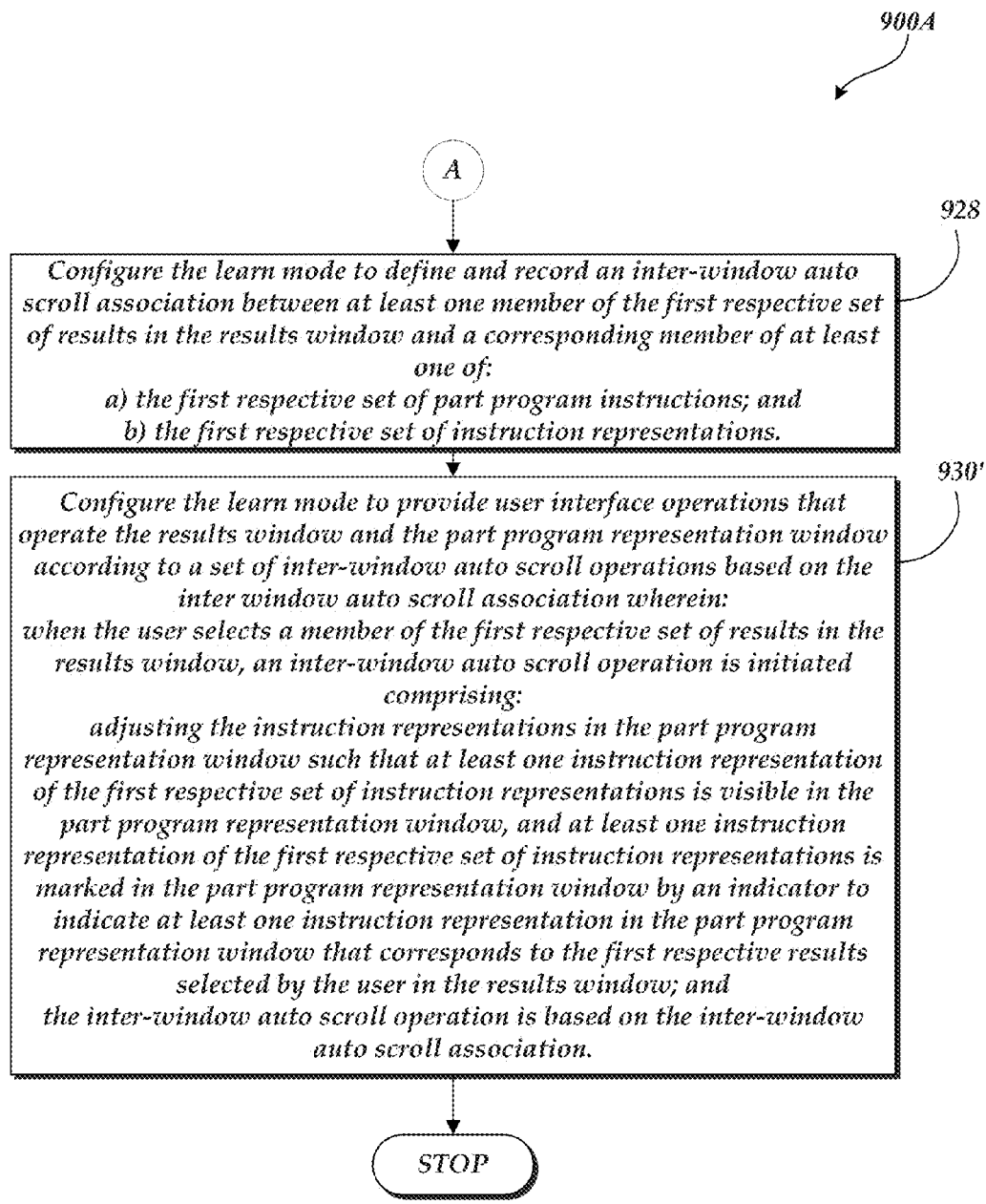
FIG. 10 is a flow diagram illustrating a routine which is an alternative to a portion of the routine of FIG. 9.

In at least one embodiment or implementation, the routine continues either to a routine portion described in block 930 or in another embodiment or implementation to an alternative block A corresponding to a routine portion, which is described in FIG. 10.

As shown in the implementation at the block 930, the learn mode is configured to provide user interface operations that operate the results window and the part program representation window (the editing window) according to a set of inter-window auto scroll operations wherein: when the user selects a member of the first respective set of results in the results window, an inter-window auto scroll operation is initiated comprising: adjusting the instruction representations in the editing window such that at least one instruction representation of the first respective set of instruction representations is visible in the part program representation window, and at least one instruction representation of the first respective set of instruction representations is marked in the editing window by an indicator to indicate at least one instruction representation in the editing window that corresponds to the first respective results selected by the user in the results window.

FIG. 10 is a flow diagram illustrating a routine portion 900A, which is an alternative to the block 930 of FIG. 9, including a particular implementation that provides a similar or identical function. If the routine portion 900A is used in place of the block 930, then after block 920 and/or block 925 as illustrated in FIG. 9 at a block 928, the learn mode is configured to define and record an inter-window auto scroll association between the at least one member of the first respective set of results in the results window and a corresponding member of at least one of:

(a) the first respective set of part program instructions; and (b) the first respective set of instruction representations.

The corresponding member is associated with part program instructions that generate the first respective set of results in the results window when executed, as outlined previously. Then, at a block 930', the learn mode is configured to provide user interface operations that operate the results window and the editing window according to a set of inter-window auto scroll operations based on the inter-window auto scroll association, wherein: when the user selects a member of the first respective set of results in the results window, an inter-window auto scroll operation is initiated comprising: adjusting the instruction representations in the editing window such that at least one instruction representation of the first respective set of instruction representations is visible in the part program representation window, and at least one instruction representation of the first respective set of instruction representations is marked in the editing window by an indicator to indicate at least one instruction representation in the editing window that corresponds to the first respective results selected by the user in the results window. The inter-window auto scroll operation is based on the inter-window auto scroll association. The inter-window auto scroll association may be established as outlined previously and/or as described below.

Figure 11:
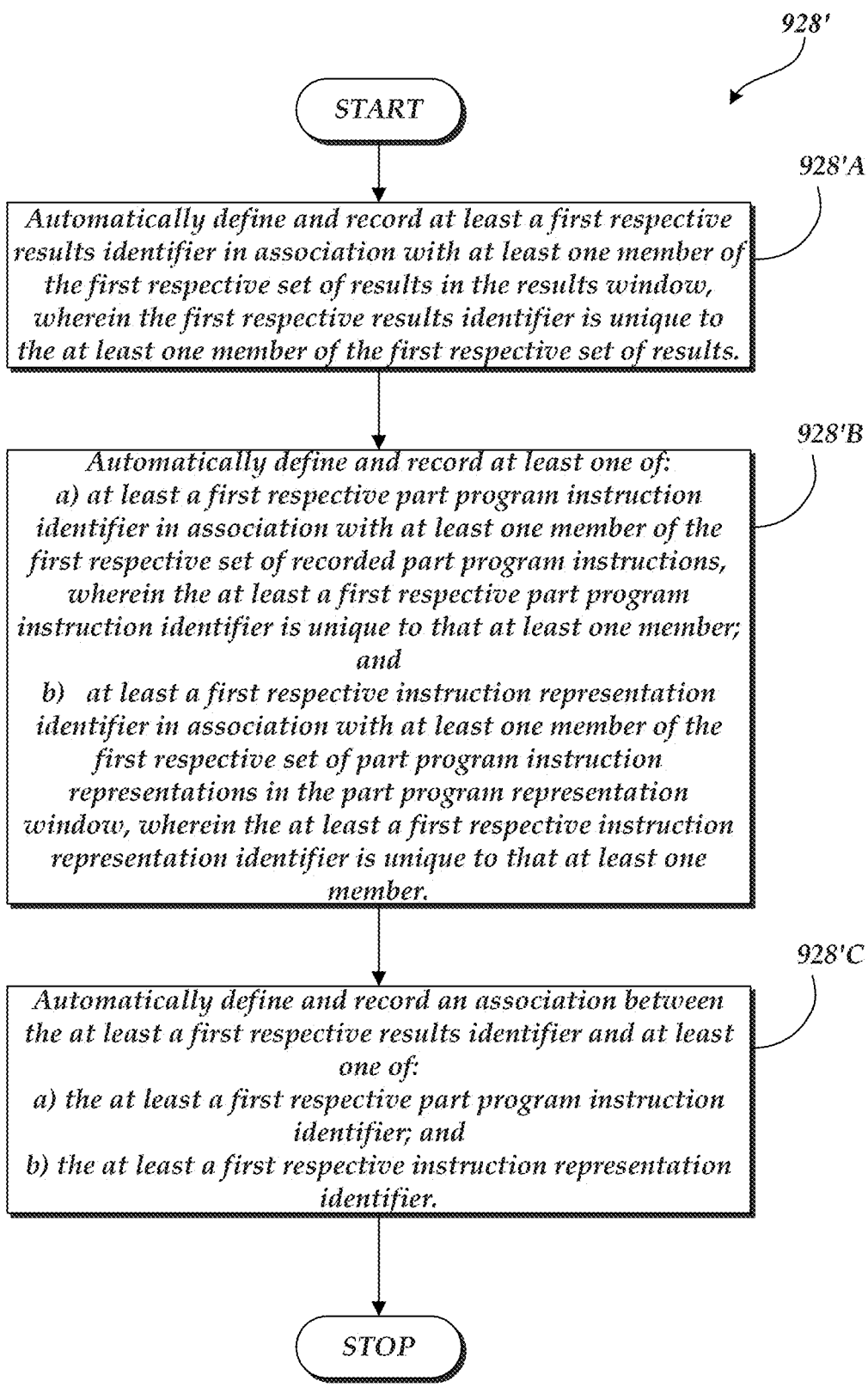
FIG. 11 is a flow diagram illustrating one embodiment of a portion of the routine of FIG. 10.

FIG. 11 is a flow diagram 928' illustrating one embodiment of a portion of the routine of FIG. 10. In particular, FIG. 11 shows one embodiment of operations usable to define and record an inter-window auto scroll association, such that it may be used to identify corresponding elements in the applicable windows.

At a block 928'A, at least a first respective results identifier is automatically defined and recorded in association with at least one member of the first respective set of results in the results window, wherein the first respective results identifier is unique to the at least one member of the first respective set of results.

At a block 928'B, at least one of the following is automatically defined and recorded:

(a) at least a first respective part program instruction identifier in association with at least one member of the first respective set of recorded part program instructions, wherein the at least a first respective part program instruction identifier is unique to that at least one member; and (b) at least a first respective instruction representation identifier in association with at least one member of the first respective set of part program instruction representations in the editing window, wherein the at least a first respective instruction representation identifier is unique to that at least one member.

At a block 928'C, an association between the at least a first respective results identifier and at least one of the following is automatically defined and recorded:

(a) the at least a first respective part program instruction identifier; and (b) the at least a first respective instruction representation identifier.

In other words, following principles previously outlined with reference to block 928 in FIG. 10, the association that is defined and recorded is between the identifier of a particular set of results in the results window and the identifier of a corresponding set of part program instructions that generate the first respective set of results in the results window when executed. In one embodiment, the identifier(s) may be implemented as outlined above with reference to FIG. 8.

As previously indicated, the results window and/or the client window and/or the part program representation window (that is, the editing window) may generate their own element identifiers at the time that they generate their displayed elements, and pass this information to the inter-window auto scroll portion, which may form an association between the various identifiers in a stored identifier association table, or the like. It should be appreciated that in some embodiments, the part program instructions in the part program instruction representations may be handled within a single application or subroutine of the machine vision inspection system control software, such that a part program instruction or its corresponding part program instruction representation may be represented by a single identifier which is usable by the inter-window auto scroll portion in relation to either of these elements. Thus, in some embodiments, the identifier associated with the results and the identifier associated with the corresponding part program instructions may be the same identifier, and the association operation outlined above with reference to block 928'C is accomplished by simply using the same identifier to identify corresponding elements in various windows.

Figure 12:
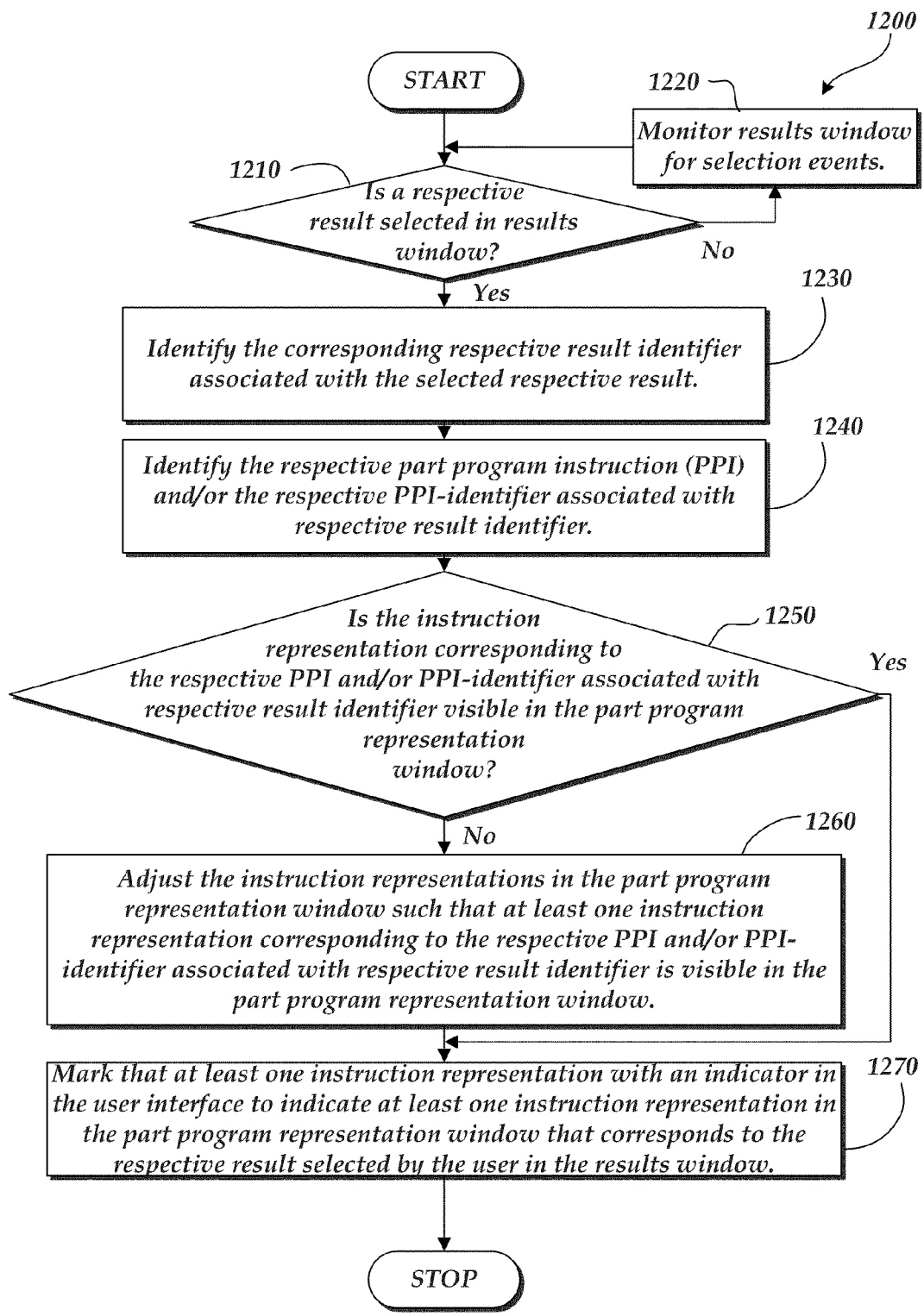
FIG. 12 is a flow diagram illustrating one embodiment of another portion of the routine of FIG. 10.

FIG. 12 is a flow diagram 1200 illustrating one embodiment of a portion of routines of FIGS. 9 and/or 10. In particular, FIG. 12 shows one embodiment of operations usable to implement the operations of blocks 930 and/or 930'.

At a decision block 1210, a decision is made as to whether a respective result is selected in the result window (e.g., by a user selecting the result through the user interface). If a respective result is not selected in the result window, the routine continues to a block 1220 where the result window is monitored for selection events, and the routine returns to the decision block 1210. If a respective result is selected in the result window, the routine continues to a block 1230.

At the block 1230, the corresponding respective result identifier associated with the selected respective result is identified.

At a block 1240, the respective part program instruction (PPI) and/or the respective PPI identifier associated with the respective result identifier is identified. In one embodiment, this may be accomplished through the intermediate step of identifying a respective part program instruction representation identifier associated with the respective result identifier, and then identifying the part program instruction(s) (PPI) underlying that respective part program instruction representation.

At a decision block 1250, a determination is made whether the instruction representation corresponding to the respective PPI and/or PPI-identifier associated with the respective result identifier is visible in the part program representation window. If the instruction representation corresponding to the respective PPI and/or PPI-identifier associated with the respective result identifier is visible in the part program representation window, the routine continues to a block 1270. If the instruction representation corresponding to the respective PPI and/or PPI-identifier associated with the respective result identifier is not visible in the part program representation window, the routine continues to a block 1260.

At a block 1260, the instruction representations in the part program representation window are adjusted such that at least one instruction representation corresponding to the respective PPI and/or PPI-identifier associated with the respective result identifier is visible in the part program representation window.

At a block 1270, that instruction representation corresponding to the respective PPI and/or PPI-identifier is marked with an indicator in the user interface to indicate at least one instruction representation in the editing window that corresponds to the respective result selected by the user in the results window.

Figure 13:
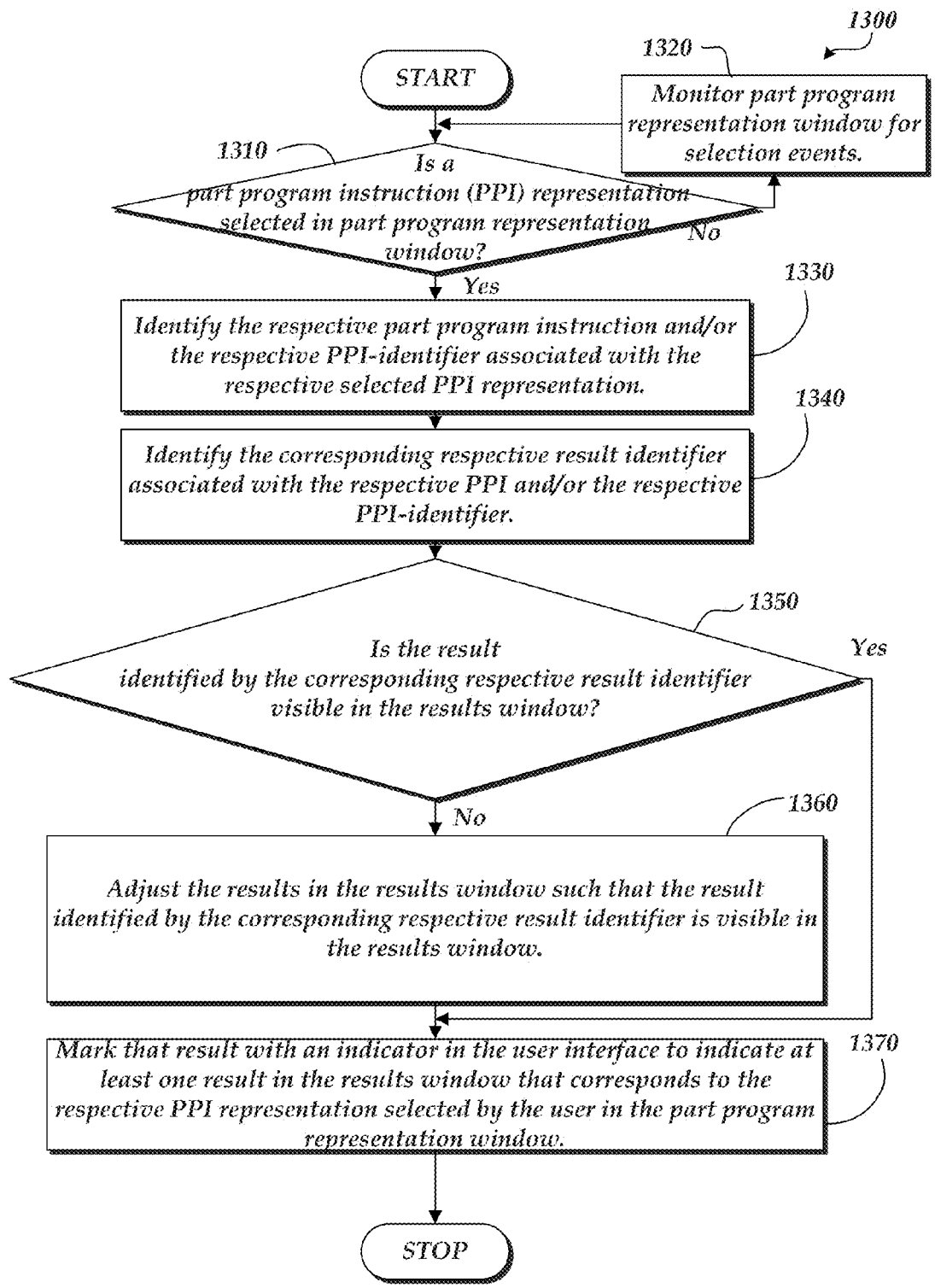
FIG. 13 is a flow diagram illustrating one embodiment of an additional and/or alternative routine for operating a program editing environment.

FIG. 13 is a flow diagram 1300 illustrating one embodiment of an additional and/or alternative routine for operating a program editing environment. In particular, FIG. 13 shows one embodiment of operations wherein a selection event in the editing window triggers identification of the corresponding results in a results window.

At a decision block 1310, a decision is made as to whether a part program instruction (PPI) representation is selected in the part program representation window. If a PPI representation is selected in the part program representation window, the routine continues to a block 1320 where the part program representation window is monitored for selection events, and the routine returns to the decision block 1310. If a PPI representation is selected in the editing window, the routine continues to a block 1330.

At a block 1330, the respective part program instruction and/or the respective PPI-identifier associated with the respective selected PPI representation is identified.

At the block 1340, the corresponding respective result identifier associated with the respective PPI and/or the respective PPI-identifier is identified.

At a decision block 1350, a determination is made whether the result identified by the corresponding respective result identifier is visible in the results window. If the result identified by the corresponding respective result identifier is visible in the results window, the routine continues to a block 1370. If the result identified by the corresponding respective result identifier is not visible in the results window, the routine continues to a block 1360.

At a block 1360, the results in the results window are adjusted such that the result identified by the corresponding respective result identifier is visible in the results window.

At a block 1370, that result is marked with an indicator in the user interface to indicate at least one result in the result window that corresponds to the respective PPI representation selected by the user in the part program representation window.

FIGS. 4-8 show a field of view display 480 that displays a field of view of the machine vision inspection system 100 as imaged by the camera 260, and for reference, schematically displays in dashed outline the location where a box tool region of interest (e.g., the box tool 482 corresponding to the box tool instruction representation 422A, and the box tool 481 corresponding to the box tool instruction representation 421A) would appear as it is defined and recorded by a user. It should be appreciated that in some embodiments, the field of view display 480 may behave as a window synchronized to display elements corresponding to elements selected or highlighted in the part program representation window (and/or other windows) in a manner analogous to that previously described herein. That is, when a part program instruction representation (e.g., a box tool instruction representation) is chosen in the editing window, the field of view display 480 may display the corresponding workpiece feature initially used to define that instruction.

In some embodiments, the displayed image may be a saved image that is recalled. The previously incorporated '232 application discloses editing portion operations wherein "surrogate data" is saved after the execution of part program instructions in learn mode. Such surrogate data may comprise a workpiece image that is saved so that it may be displayed in the field of view display 480 when a corresponding part program instruction representation (e.g., a box tool instruction representation) is chosen in the editing window (that is, when the workpiece feature in that image was used to initially define that instruction). Alternatively, the surrogate data may provide the means of determining the physical location, lens configuration, and lighting, etc., to speed up actual duplication of the image acquisition conditions and image used when initially defining the instruction. As described in the '232 application, this procedure may save considerable time and avoid collision risk, in contrast to requiring adjustment of the actual vision machine components to acquire a new image of that workpiece feature. More generally, the editing portion operations described in the '232 application may advantageously be used in combination with various embodiments disclosed herein to provide the proper program editing context, either by surrogate mode execution or actual mode execution, or a combination of both, when appropriate after an auto scroll operation described herein is executed. Therefore, portions of the '232 application are included below with FIGS. 14-19, for easy reference and understanding. Further understanding may be gained from the '232 application and other incorporated references.

Figure 14:
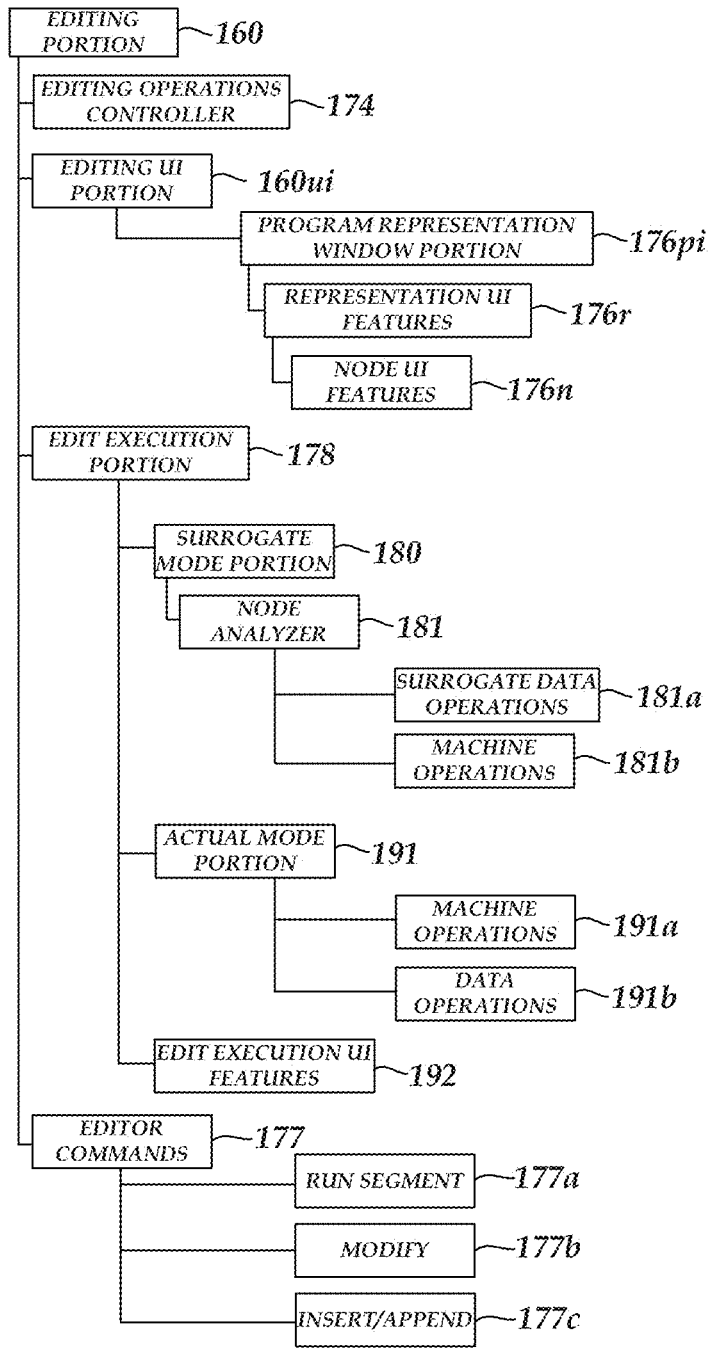
FIG. 14 is block diagram illustrating additional components of the editing portion 160 of FIG. 2.

FIG. 14 is a block diagram illustrating additional components of the editing portion 160 of FIG. 2. As shown in FIG. 14, the editing portion 160 includes an editing operations controller 174, an editing user interface portion 176, an editor commands portion 177, and an edit execution portion 178. The editing operation controller 174 controls the operations for the editing functions, and the editing user interface portion 176 provides the user interface features for the editing functions. The editing user interface portion 176 includes a program representation window portion 176pi, which includes representation user interface features 176r, which includes node user interface features 176n. The program representation window portion 176pi provides a part program representation including part program instruction representations, as will be described in more detail below with respect to FIG. 15. In one embodiment, the part program representation may be provided in a tree structure. The representation user interface features 176r provides features such as an insertion pointer which may change color depending on the state of the context and how the context was obtained (e.g., whether the context was produced from surrogate data, by an actual run, etc.). With regard to the node user interface features 176n, in one embodiment, these may include features such as icons or broken icons, and color highlights, so as to indicate if a node is active, etc.

The edit execution portion 178 is responsible for various execution modes during an editing process, and includes a surrogate mode portion 180, an actual mode portion 191, and an edit execution user interface features portion 192. The surrogate mode portion 180 includes a node analyzer 181, which includes surrogate data operations 181A and machine operations 181B. As will be described in more detail below, when the surrogate mode portion 180 operates a surrogate execution mode, in accordance with the present invention, surrogate data is utilized for generating context for the continuing editing operations. The node analyzer 181 in one implementation determines whether the part program execution has reached the target node (e.g., where a modification is to be made in the part program). The node analyzer 181 determines whether the surrogate data operations 181A or actual machine operations 181B will be performed, in accordance with the type of node that is involved. In general, once the target node is reached, then actual machine operations are performed, wherein for part program instructions prior to the target node, surrogate data operations may be utilized for generating at least some of the context that is needed for the continuing editing operations. If surrogate data is missing, a user may be prompted to allow/perform actual machine operations to generate the needed context. In one implementation, each node is analyzed to determine if surrogate data operations are applicable, including whether surrogate data exists, if it is the right type of node for surrogate data operations, alternatively whether actual machine operations need to be utilized, etc.

The actual mode portion 191 includes operations that are more traditionally performed by prior machine vision systems. It will be appreciated that the actual mode portion 191 may also be called by the surrogate mode portion 180 for performing the machine operations 181B, when appropriate. The actual mode portion 191 includes machine operations 191A and data operations 191B. The machine operations 191A perform actual machine operations (e.g., moving the stage as part of a video tool operation), while the data operations 191B generally output data. The edit execution user interface features 192 provide user interface features for the execution of the editing functions (e.g., indications as to the status of various execution operations, such as color codes indicating what portions of a part program have utilized surrogate data, or have been run through an actual execution, etc.).

The editor commands 177 includes a run segment portion 177A, a modify portion 177B, and an insert/append portion 177C, described in detail in the '232 application. In general, the run segment portion 177A performs an actual run of a selected segment of the part program. It will be appreciated that in order to run a selected segment of a part program, the proper context up to the selected segment must be established. As will be described in more detail below, in accordance with the present invention, the proper context may be established by utilizing surrogate data. If surrogate data does not exist for a certain portion of a part program, then a segment may be run so as to generate the needed surrogate data. It will be appreciated that in prior machine vision systems, it has been difficult to run an isolated segment of a part program without running all of the preceding portions of the part program, due to the need for the proper context leading up to the selected segment. For example, if the segment required the stage to be lowered, but the system was unaware of the present X-Y-Z location of the stage, then lowering the stage to an unknown position could be inadvisable. Thus, in prior implementations, the technique typically utilized was to run the entire part program from the beginning in order to be able to run a segment in the middle, for which all of the preceding operations could require a significant amount of time to perform. In contrast, in accordance with the present invention, surrogate data may be utilized to establish the proper context for making edits to or running a segment of a part program without requiring the running of the entire part program from the beginning.

The modify portion 177B has certain similarities to the operation of the run segment portion 177A. In general, when an instruction representation in a part program is selected to be modified, then the surrogate mode may be utilized for the portions of the part program that precede the instruction that is to be modified. In one embodiment, when the modify command is selected for an instruction representation in a part program, the node for the instruction representation is designated as the target node. Once the target node is reached, the editor switches out of the surrogate mode and switches into the actual execution mode (e.g., as controlled by the actual mode portion 191) and executes the first relevant part program instruction of the node. In one embodiment, if the instruction that is selected for modification corresponds to a child node, then the actual execution may be designated to begin at the parent node. In one specific example embodiment, if a child node related to a box tool is to be modified, the parent node, which involves setting up the image acquisition for the box tool, may be the node at which the actual execution is set to begin. With regard to the insert/append component 177C, if the insert is in between child nodes, then the parent node may also need to be executed in order to perform the desired insertion. It will be appreciated that in certain implementations an append operation may generally be considered to be a special case of an insert operation, which occurs at the end of an existing part program.

Figure 15:
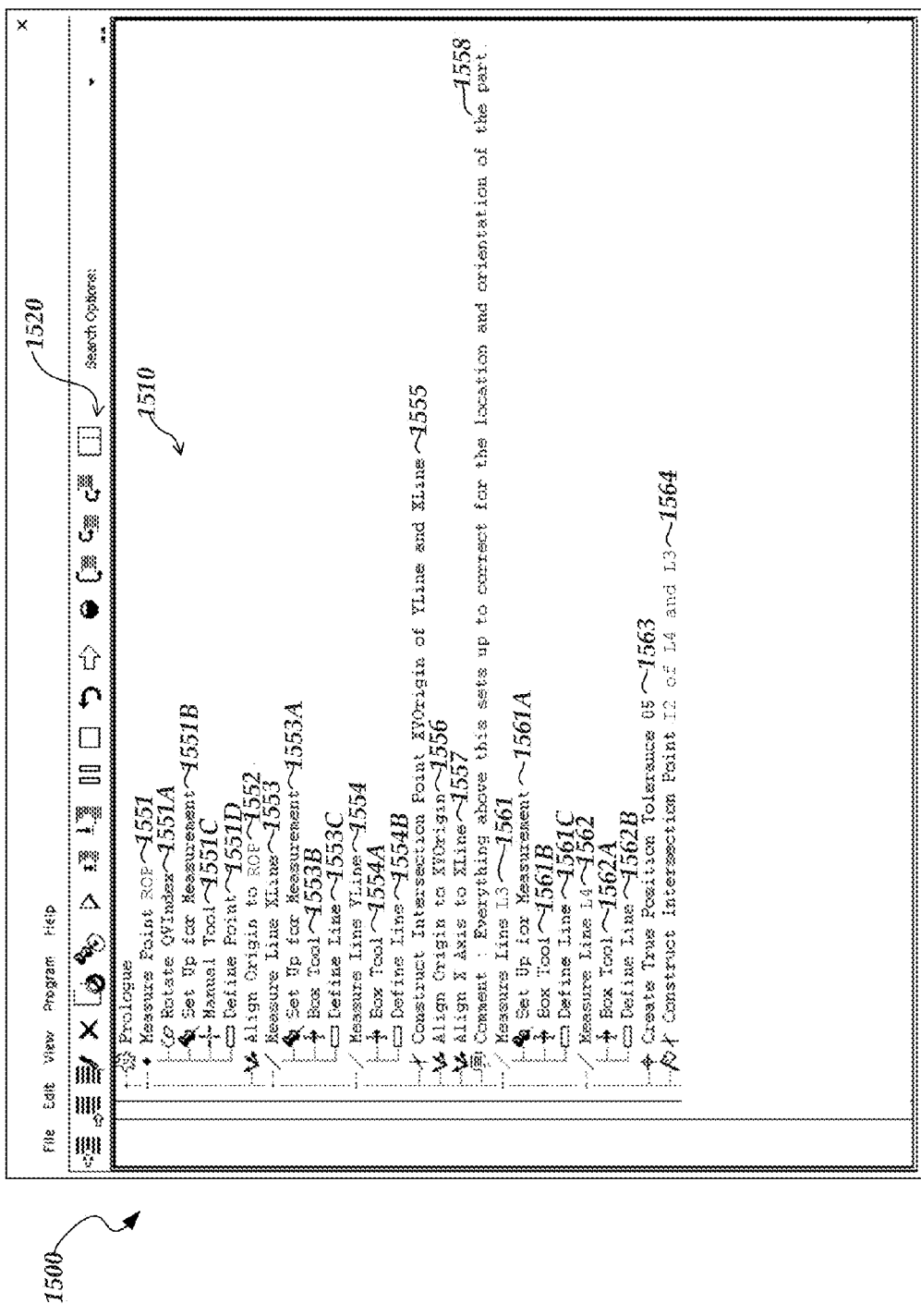
FIG. 15 is a diagram of an editing interface including a part program representation that has a plurality of instruction representations.

FIG. 15 is a diagram of an editing interface 1500 including a representation of a part program 1510 that has a plurality of initial part program instruction representations 1551-1564. The editing interface 1500 also includes various measurement and/or operation selection bars such as the selection bar 1520. The operation of the specific instruction representations of the part program representation 1510 will be described in more detail below with respect to FIG. 16.

Figure 16:
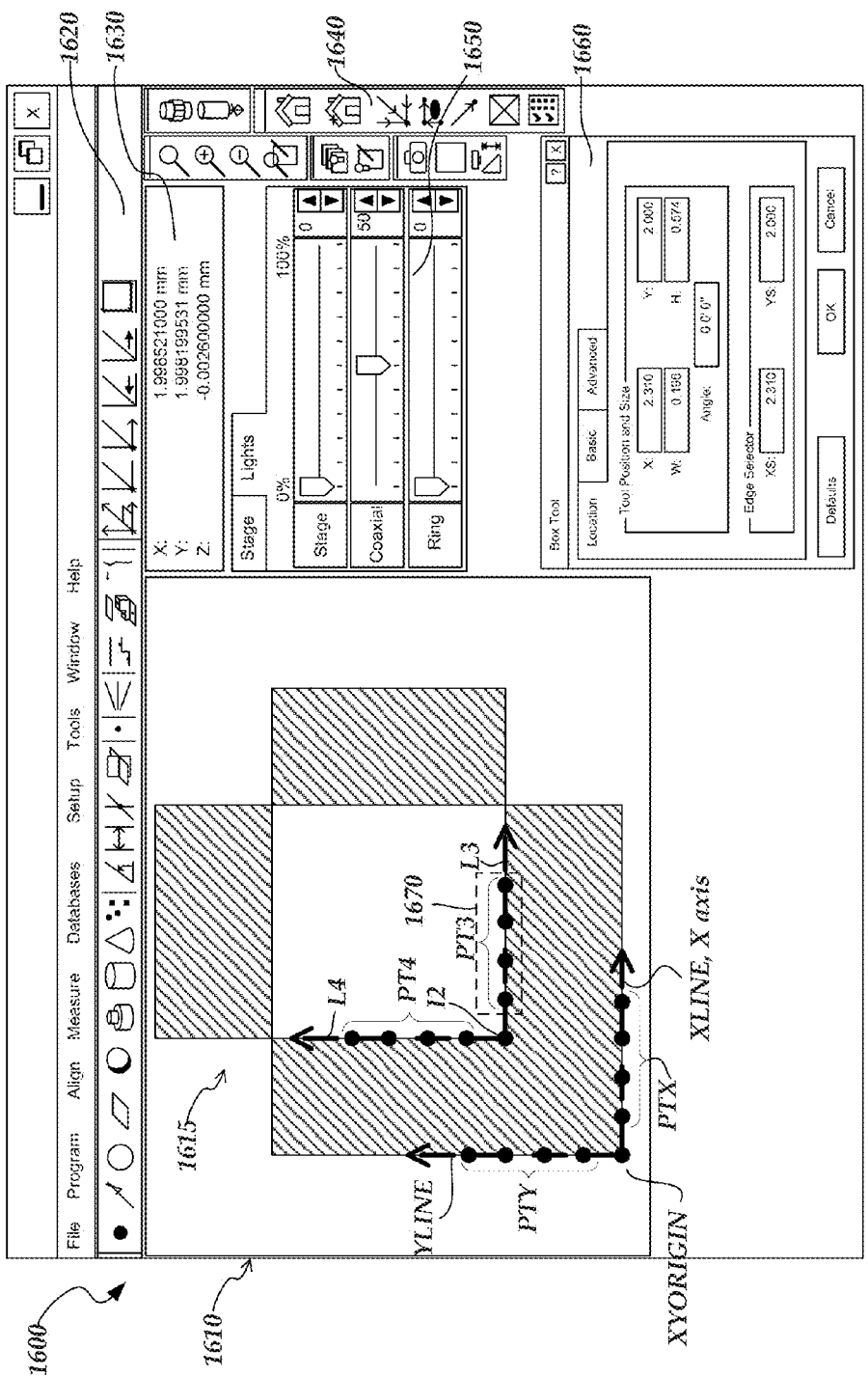
FIG. 16 is a diagram of a user interface including an image of a workpiece on which the part program corresponding to FIG. 15 has been performed.

FIG. 16 is a diagram illustrating a user interface 1600 including an image of a field of view window 1610 with a workpiece 1615, on which the part program corresponding to FIG. 15 has been performed. The user interface 1600 also includes various measurement and/or operation selection bars such as the selection bars 1620 and 1640, a real-time X-Y-Z (position) coordinate window 1630, a light control window 1650, and a video tool parameter box 1660. As will be described in more detail below, various features on the workpiece 1615 are determined in accordance with related part program instruction representations of FIG. 15, such as sets of edge points PTX, PTY, PT3, and PT4, lines XLINE, YLINE, L3, and L4, an origin point XYORIGIN, and an intersection point I2.

The following description will make reference to both the initial part program instruction representations 351-364 of FIG. 15, and the corresponding features on the workpiece 1615 of FIG. 16. In one embodiment, each of the instruction representations 351-364 is associated with a node, and is assigned a node number or identifier. In certain implementations, a tree-structure is utilized, wherein some of the instruction representations are associated with parent nodes, and some are associated with children nodes. For example, the children node instruction representations 1551A-1551D, 1553A-1553C, 1554A-1554B, 1561A-1561C, and 1562A-1562B are associated with parent node instruction representations 1551, 1553, 1554, 1561, and 1562, respectively. It will also be appreciated that in one embodiment, the instruction representations 1551-1564 as displayed in the editing interface 1500 comprise icons and labels derived from the mark up language instructions of the part program. In one embodiment, the mark up language of the part program may comprise XML-like code. The instruction representations 1551-1564 thus point to associated code instructions that are executed, as will be described in more detail below with respect to FIGS. 17A and 17B.

As shown in FIG. 15, the part program representation 1510 begins with the instruction representations 1551 and 1552, which indicate that the user manually selects a location on the workpiece 1615 to act as a rough origin point ROP (not shown), and then aligns the origin to the rough origin point ROP. More specifically, the instruction representations 1551A, 1551B, 1551C, and 1551D indicate that the user sets up and utilizes a manual tool to define the rough origin point ROP and the instruction representation 1552 aligns the origin with the rough origin point ROP. The instruction representation 1553 then indicates that a box tool will be opened for measuring the line XLINE. More specifically, the instruction representations 1553A and 1553B indicate that the user sets up (e.g., including moving the stage to a designated location and acquiring a corresponding image) and utilizes the box tool to determine the edge points PTX. The functions and operations of box tools and other edge detection video tools are known in the art and are described in more detail in the previously incorporated references. The edge points PTX that are determined by the box tool are then utilized by the instruction representation 1553C to define the line XLINE. Similarly, the instruction representation 1554 indicates that a box tool will be opened for measuring the line YLINE, wherein the instruction representation 1554A indicates that the user utilizes the box tool to determine the edge points PTY, which are then utilized as indicated by the instruction representation 1554B to define the line YLINE.

The instruction representation 1555 then indicates that an intersection point XYORIGIN is determined at the intersection of the lines XLINE and YLINE. The instruction representation 1556 then indicates that the machine vision system is commanded to align the origin to the point XYORIGIN. The instruction representation 1557 then indicates that the machine vision system is commanded to align the X axis for the workpiece 1615 to the line XLINE. As will be described in more detail below with respect to FIG. 5, and as indicated by the comment line 1558, the operations of the instruction representations 1551-1557 establish the correct location and orientation of the workpiece 1615 for performing additional measurements.

The instruction representation 1561 then indicates that a box tool will be opened for measuring the line L3. More specifically, the instruction representations 1561A and 1561B indicate that the user sets up (e.g., including moving the stage to a designated location and acquiring a corresponding image) and utilizes the box tool to determine the edge points PT3, which are then utilized as indicated by the instruction representation 1561C to define the line L3. As will be described in more detail below, the box tool utilized for measuring the line L3 (i.e., illustrated as box tool 1670 in FIG. 16), and the associated instruction representations 1561 and 1561A-1561C, are utilized as examples in FIGS. 17A and 17B for illustrating how surrogate data is generated, stored, and modified.

Returning to FIG. 15, the instruction representation 1562 indicates that a box tool will be opened for measuring the line L4, wherein the instruction representation 1562A indicates that the user utilizes a box tool to determine the edge points PT4, which are then utilized as indicated by the instruction representation 1562B to define the line L4. The instruction representation 1563 indicates that the user defines a selected position tolerance and the instruction representation 1564 indicates that an intersection point 12 is determined where the previously determined lines L3 and L4 intersect.

After the part program corresponding to the representation 1510 is stored and exited, when the part program is recalled for editing, prior implementations have required that the entire part program be executed from the beginning, in order to produce valid context for continuing edits to the part program. While prior implementations have produced accurate results and part programs by executing all of the instructions each time a part program is recalled for editing, the execution of all of the instructions may take a significant amount of time (particularly those instructions that require certain time consuming processes such as hardware interactions, etc.). As will be described in more detail below, in accordance with the present invention, rather than executing the entire part program from the beginning, previously saved data may be used as surrogate data for simulating valid context for continuing edits to the part program.

In other words, in one embodiment, when continuing edits are being made to the part program for making measurements on the workpiece 1615, it is useful to know certain parameters. For example, in order to know the correct thresholds, size, and location for a video tool, it is necessary to have the right video image, including information such as the correct stage position, light levels, magnification, etc. In one embodiment, such information may be considered as part of the "hardware context." In addition, in order to know if a sequence is correct for continuing edits to the part program, it is useful to know what has been done already, including what features have been measured, what part coordinate system is being utilized, etc. In one embodiment, this information may be considered as part of the software context. In one embodiment, the context is generally considered as establishing the user interface of the machine vision inspection system in a state such that all of the native interface control elements are ready for modifying the part program. As noted above, accurate context is provided at the time the part program is initially recorded, and also later at runtime, in that all of the part program instructions (e.g., corresponding to the representations 1551-1564) are generally executed in order. As noted above, this provides a valid context for continuing edits to the part program, including indicating any measurements and results already produced by the part program (e.g. the indications of the lines XLINE, YLINE, L3, L4, and intersection points XYORIGIN and I2 as illustrated with respect to the workpiece 1615 in the user interface 1600).

As will be described in more detail below, when editing a part program, rather than being required to execute all of the instruction representations of the part program in order to generate the needed context, certain context can be simulated by using previously saved data as surrogate data. Briefly, during the recording or runtime execution of a part program, the data that is needed to determine context is stored with the part program. Then, at a later time, certain results may be simulated utilizing the saved data as surrogate data in order to produce the desired context. Thus, by avoiding the execution of certain time consuming operations (e.g., those requiring hardware interaction such as the moving of the stage, edge detection, focusing, lighting changes, pattern matching, etc.), significant time savings may be achieved. The saving of data that may be later utilized as surrogate data will be described in more detail below with respect to FIGS. 17A and 17B.

FIGS. 17A and 17B are diagrams of mark up language code instructions of the part program which correspond to some of the instruction representations of FIG. 15. FIGS. 17A and 17B are diagrams 1700A and 1700B of mark up language code instructions which correspond to some of the instruction representations of the part program representation of FIG. 15. More specifically, FIGS. 17A and 17B show the part program instructions in XML-like code which correspond to the instruction representations 1561 and 1561A-1561C of FIG. 15 for measuring the line L3. It will be appreciated that in one embodiment, the instruction representations 1561 and 1561A-1561C comprise icons and labels that are derived from the XML-like code instructions of FIGS. 17A and 17B. The instruction representations 1561 and 1561A-1561C are not themselves executed, but instead point to the associated code instructions of FIGS. 17A and 17B that are executed.

As shown in FIGS. 17A and 17B, the XML-like code instructions include node I.D. numbers 1761, 1761A, 1761B, and 1761C, which in one embodiment may correspond to the instruction representations 1561, 1561A, 1561B, and 1561C of FIG. 15. The XML-like code instructions also include certain position information 1710 for the image position, and certain box tool position information 1720 for the box tool, such as may be displayed in the areas 1630 and 1660 of the user interface 1600 of FIG. 16. As shown in FIG. 17B, data 1730 is stored with the part program that may be utilized at a later time as surrogate data for simulating context. More specifically, when the instruction representation 1561B of FIG. 15 indicates that the box tool 1670 of FIG. 16 is run to determine the set of edge points PT3, the positions of the set of edge points PT3 relative to the part coordinate system for the workpiece are stored in the XML-like code instructions as the data 1730. Modifications may be made to the part program which may result in modifications to the surrogate data 1730.

Figure 18A:
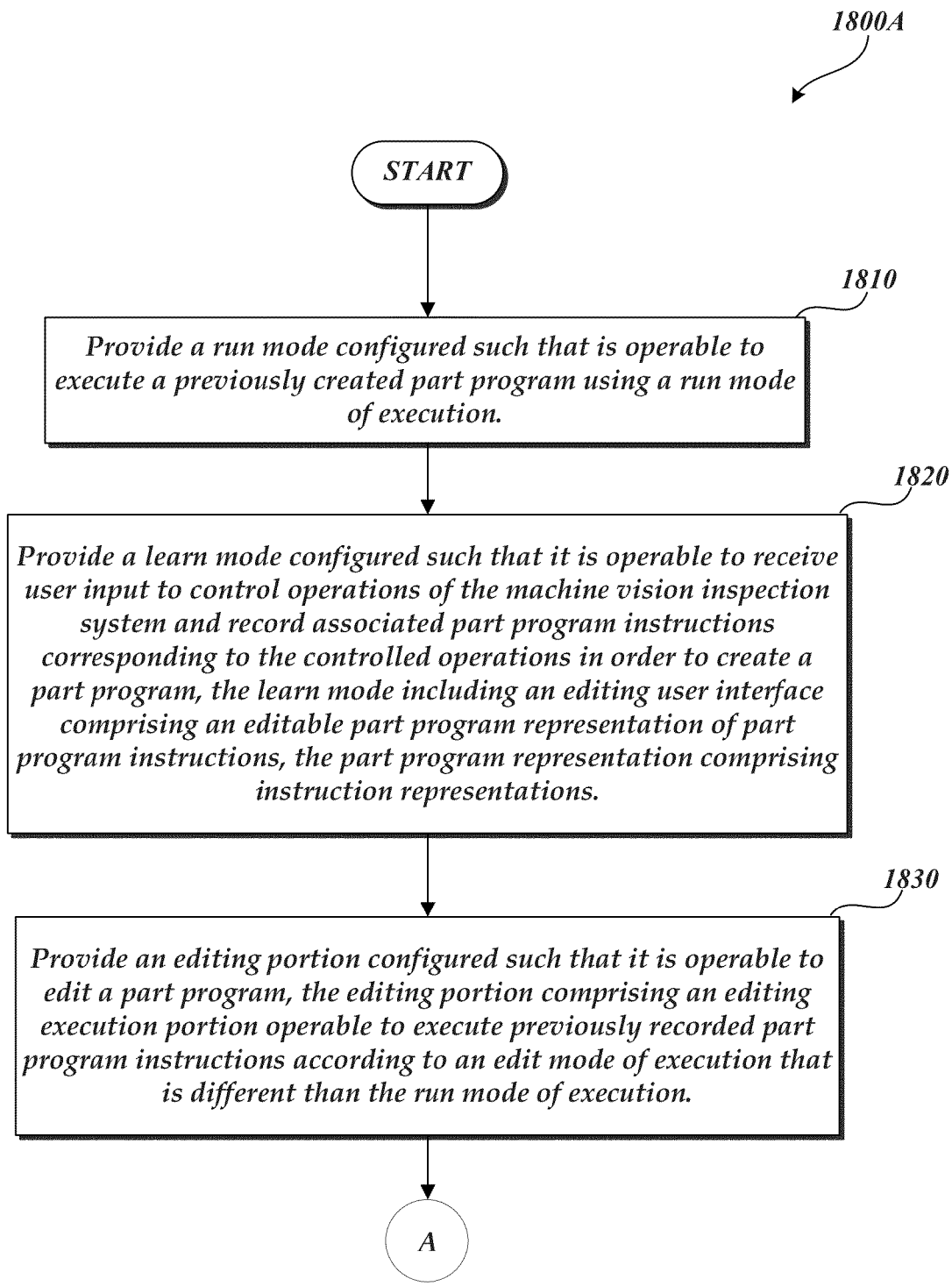
FIGS. 18A and 18B are flow diagrams illustrating one embodiment of a routine for providing a machine vision system part program editing environment that includes real time context generation features.
Figure 18B:
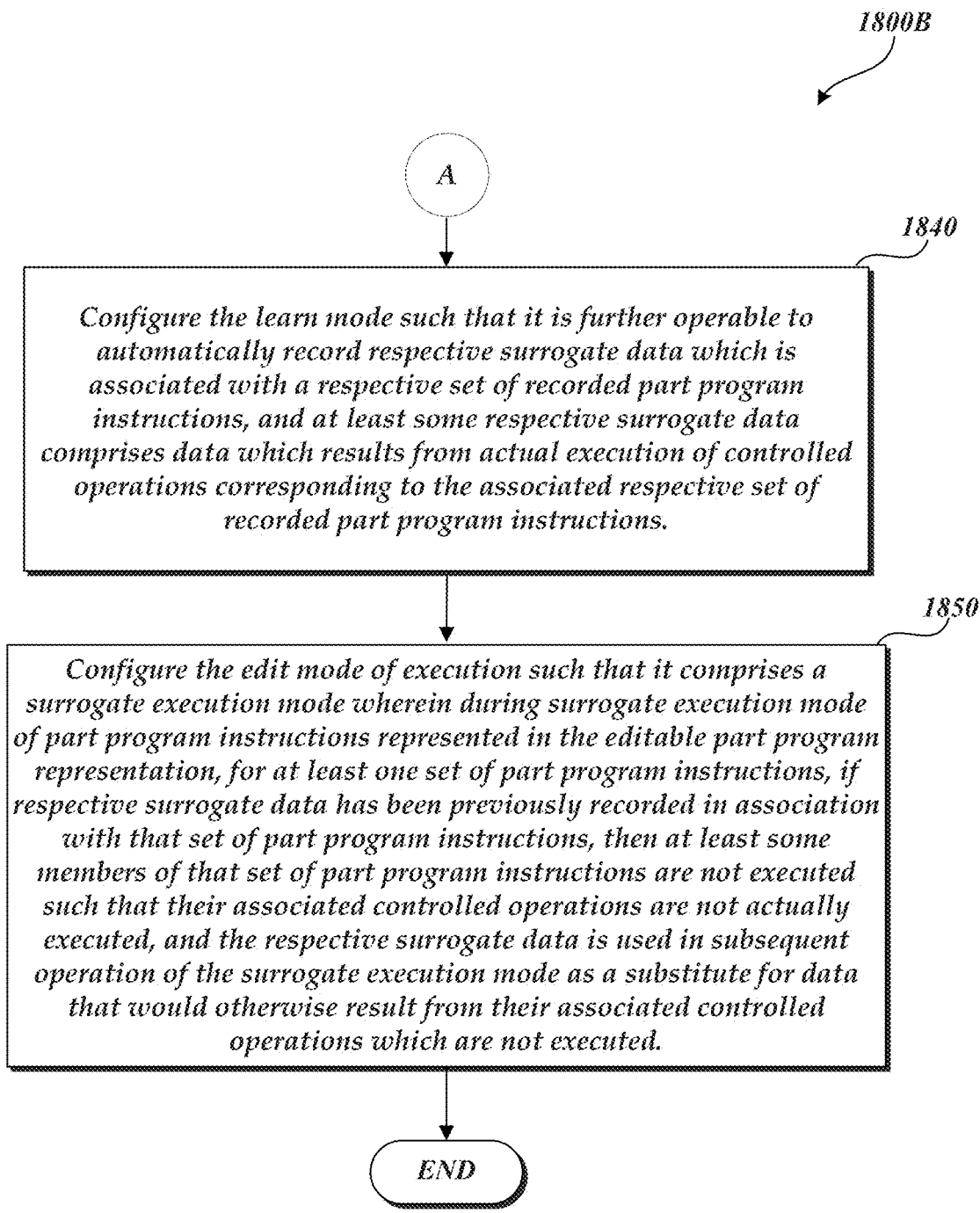

FIGS. 18A and 18B are flow diagrams illustrating one embodiment of a routine 1800 for providing a machine vision system program editing environment that includes real time context generation features. As shown in FIG. 18A, at a block 1810, a run mode is provided that is configured such that it is operable to execute a previously created part program using a run mode of execution. At a block 1820, a learn mode is provided that is configured such that it is operable to receive user input to control operations of the machine vision inspection system and record associated part program instructions corresponding to the controlled operations in order to create a part program. In addition, the learn mode is made to include an editing user interface comprising an editable part program representation of part program instructions, the part program representation comprising instruction representations. At a block 1830, an editing portion is provided that is configured such that it is operable to edit a part program. In addition, the editing portion comprises an editing execution portion operable to execute previously recorded part program instructions according to an edit mode of execution that is different than the run mode of execution. From the block 1830, the routine continues to a point A, as will be described in more detail below with respect to FIG. 18B.

As shown in FIG. 18B, from the point A, the routine continues to a block 1840. At the block 1840, the learn mode is configured such that it is further operable to automatically record respective surrogate data which is associated with a respective set of recorded part program instructions. In addition, at least some respective surrogate data comprises data which results from actual execution of controlled operations corresponding to the associated respective set of recorded part program instructions.

At a block 1850, the edit mode of execution is configured such that it comprises a surrogate execution mode wherein during surrogate execution mode of part program instructions represented in the editable part program representation, for at least one set of part program instructions, if respective surrogate data has been previously recorded in association with that set of part program instructions, then at least some members of that set of part program instructions are not executed such that their associated controlled operations are not actually executed. In addition, the respective surrogate data is used in subsequent operation of the surrogate execution mode as a substitute for data that would otherwise result from their associated controlled operations which are not executed.

Figure 19:
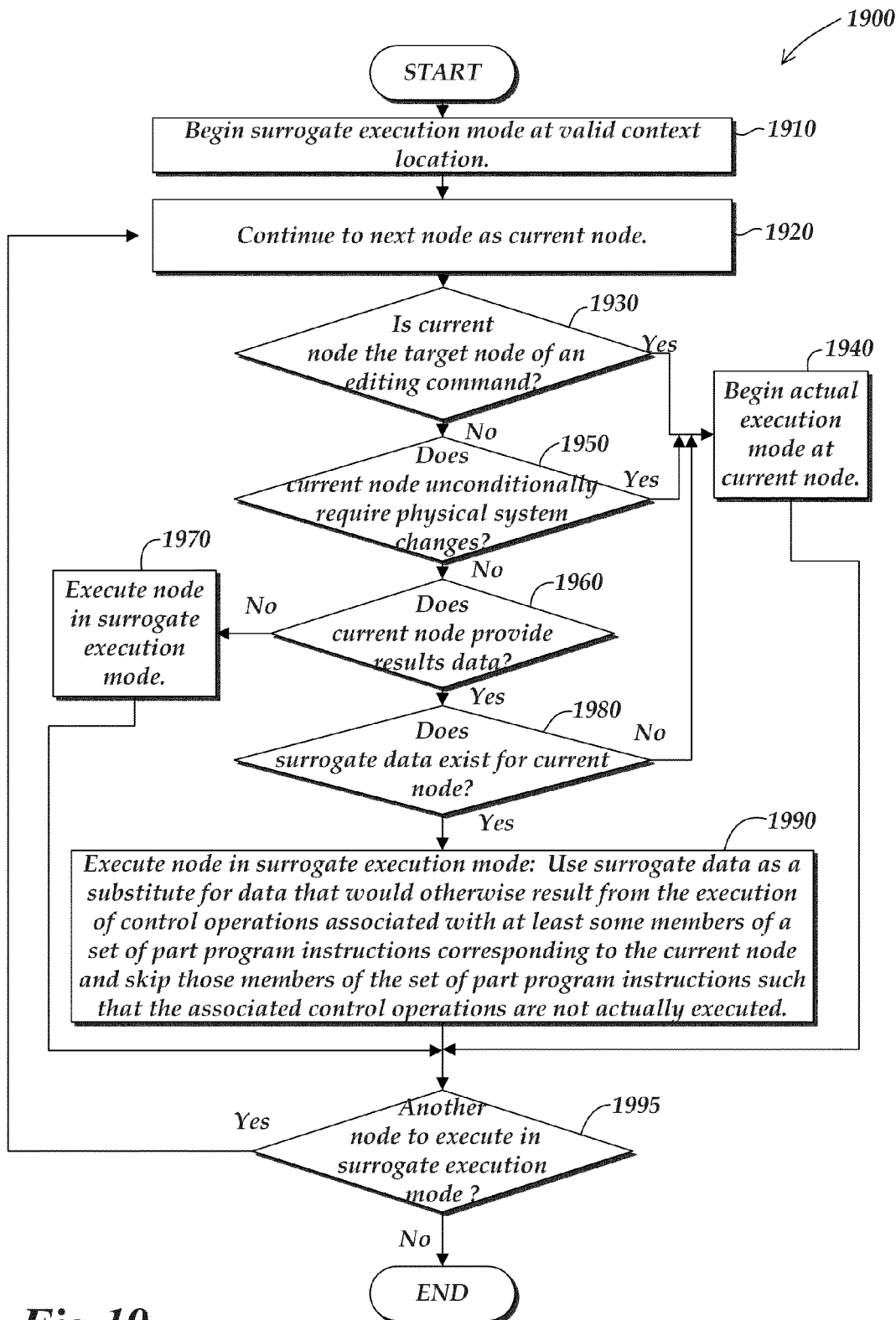
FIG. 19 is a flow diagram illustrating one embodiment of a routine for performing a surrogate execution mode in order to provide a valid editing context at a part program location indicated by part program instruction representation, element, or node.

FIG. 19 is a flow diagram illustrating one embodiment of a routine 1900 for performing a surrogate execution mode in order to provide a valid editing context at a part program location indicated by part program instruction representation, element, or node. At a block 1910, the surrogate execution mode is begun at a valid context location.

At a block 1920, the routine continues to the next node as a current node. At a decision block 1930, a determination is made as to whether the current node is the target node of an editing command. If the current node is the target node of an editing command, then the routine continues to a block 1940, where an actual execution mode is begun at the current node, after which the routine continues to a decision block 1995, as will be described in more detail below. However, in one implementation, the target node may be considered to be the parent node associated with an instruction representation, and the actual execution mode may start at the parent node such that the physical set up for measurement corresponding to an instruction representation is performed to provide the correct physical context for editing at the instruction representation.

If at the decision block 1930 it is determined that the current node is not the target node of an editing command, then the routine continues to a decision block 1950, where a determination is made as to whether the current node unconditionally requires physical system changes. For example, if the node moves the stage to image a new portion of the workpiece (e.g., a via a simple "move" command, or the like), then, in some embodiments, this may unconditionally requires physical system changes. Similarly, certain magnification changes are unconditional physical system changes, and so on. However, it will be appreciated that in some embodiments, if such changes are embedded within a parent node that already has associated surrogate data, and a subsequent node again requires a similar physical change (e.g., a move or magnification change, respectively), then it may not be unconditionally required, since it will eventually be superseded by the similar subsequent instruction. Various methods of analyzing whether a current node unconditionally requires physical system changes may be determined by one skilled in the art, based on the teachings of this disclosure. In any case, if the current node does unconditionally require physical system changes, then the routine continues to the block 1940. If the current node does not unconditionally require physical system changes, then the routine continues to a decision block 1960.

At the decision block 1960, a determination is made as to whether the current node provides results data. If the current node does provide results data, then the routine continues to a decision block 1980, as will be described in more detail below. If the current node does not provide results data, then the routine continues to a block 1970, where the node is executed in surrogate execution mode, after which the routine continues to the block 1995, as will be described in more detail below.

At the decision block 1980, a determination is made as to whether surrogate data exists for the current node. If surrogate data does exist for the current node, then the routine continues to a block 1990, as will be described in more detail below. If surrogate data does not exist for the current node, then the routine continues to the block 1940.

At the block 1990, the node is executed in surrogate execution mode. For the surrogate execution mode, surrogate data is used as a substitute for data that would otherwise result from the execution of control operations associated with at least some members of a set of part program instructions corresponding to the current node, and those members of the set of part program instructions are skipped such that the associated control operations are not actually executed.

The routine then continues to the decision block 1995, where a determination is made as to whether there is another node to execute in the surrogate execution mode. If there is another node to execute in the surrogate execution mode, then the routine returns to the block 1920, and if not, then the routine ends. For example, if execution has arrived at decision block 1995 by reaching a target node and executing blocks 1930 and 1940, then in some instances there will not be another node to execute in surrogate execution mode because the context may already be established for editing at, or within, the target node.

While various preferred and exemplary embodiments of the invention have been illustrated and described, it will be appreciated that various changes can be made therein without departing from the spirit and scope of the invention.

The embodiments of the invention in which an exclusive property or privilege is claimed are defined as follows:

1. A machine vision inspection system comprising an imaging portion, a stage for holding one or more workpieces in a field of view of the imaging portion, a control portion including a processor, a display, and a user interface, wherein the machine vision inspection system further comprises:
a run mode configured such that it is operable to execute a previously created part program using a run mode of execution;
a learn mode configured such that it is operable to receive user input to control operations of the machine vision inspection system and record associated part program instructions corresponding to the controlled operations in order to create a part program, the learn mode including a learn mode user interface comprising:
an editing user interface portion comprising an editable part program representation of part program instructions in an editing window, the part program representation comprising instruction representations; and
a results window which receives and displays respective results which comprise results provided by controlled operations of the machine vision inspection system;
wherein the learn mode is configured such that when user input is received that provides a first respective set of controlled operations of the machine vision inspection system that include operations that determine and display a first respective set of results in the results window, then the learn mode is operable to automatically provide operations comprising:
recording a first respective set of part program instructions corresponding to the first respective set of controlled operations that include operations that determine and display the first respective set of results in the results window;
display the first respective set of results in the results window; and
define and display in the editing window a first respective set of instruction representations corresponding to the first respective set of part program instructions that include operations that determine and display a first respective set of results in the results window; and
wherein the learn mode user interface is configured such that the results window and the editing window operate according to a set of inter-window auto scroll operations including:

in response to user selection of a member of the first respective set of results in the results window, an inter-window auto scroll operation is initiated comprising:
adjusting the instruction representations in the editing window such that at least one instruction representation of the first respective set of instruction representations is displayed in the editing window; and
marking at least one instruction representation of the first respective set of instruction representations displayed in the editing window with an indicator to indicate that it corresponds to the member of the first respective results selected by the user in the results window.

2. The machine vision inspection system of claim 1, wherein the learn mode is configured to define and record an inter-window auto scroll association used to identify corresponding elements in a plurality of windows comprising the editing window and the results window.

3. The machine vision inspection system of claim 2, wherein the inter-window auto scroll association comprises:
a respective part program instruction identifier that is automatically defined and recorded in association with at least one respective member of the first respective set of recorded part program instructions or their set of instruction representations;
a respective results identifier that is automatically defined and recorded in association with at least one member of the first respective set of results in the results window that corresponds to the at least one respective member of the first respective set of recorded part program instructions or their set of instruction representations; and
an association defined between the respective results identifier and the respective part program instruction identifier.

4. The machine vision inspection system of claim 3, wherein the association defined between the respective results identifier and the respective part program instruction identifier is defined by using the same identifier for each.

5. The machine vision inspection system of claim 3, wherein the first respective set of recorded part program instructions comprises instructions written in a mark up language, and the respective part program instruction identifier that is automatically defined and recorded comprises an identifier that is automatically generated and inserted into a part program instruction.

6. The machine vision inspection system of claim 1, wherein the learn mode user interface is configured such that the results window and the editing window operate according to a set of inter-window auto scroll operations including:
in response to user selection of a member of the first respective set of instruction representations in the editing window, an inter-window auto scroll operation is initiated comprising:
adjusting the results in the results window such that at least one member of the first respective set of results is displayed in the results window; and
marking at least one member of the first respective set of results displayed in the results window with an indicator to indicate that it corresponds to the member of the first respective set of instruction representations selected by the user in the editing window.

7. The machine vision inspection system of claim 1, wherein marking the at least one instruction representation with an indicator comprises highlighting the at least one instruction representation.

8. The machine vision inspection system of claim 1, wherein the inter-window auto scroll operation that is initiated further comprises transferring control to the editing window such that editing operations are immediately facilitated.

9. The machine vision inspection system of claim 8, wherein transferring control to the editing window such that editing operations are immediately facilitated comprises selection of the at least one instruction in the editing window that corresponds to the member of the first respective results selected by the user in the results window.

10. The machine vision inspection system of claim 1, wherein the learn mode user interface further comprises a client window which displays elements defined by controlled operations of the machine vision inspection system; and wherein the learn mode is configured such that when user input is received that provides a client-affecting set of controlled operations of the machine vision inspection system that include operations that define a first respective element displayed in the client window, then the learn mode is operable to automatically provide operations comprising:

recording a client-affecting set of part program instructions corresponding to the client-affecting set of controlled operations that include operations that define the first respective element displayed in the client window; and define and display in the editing window a client-affecting set of instruction representations corresponding to the client-affecting set of part program instructions that include operations that define the first respective element displayed in the client window; and wherein the learn mode user interface is configured such that the client window and the editing window operate according to a set of inter-window auto scroll operations including:

in response to user selection of the first respective element displayed in the client window, an inter-window auto scroll operation is initiated comprising:

adjusting the instruction representations in the editing window such that at least one instruction representation of the client-affecting set of instruction representations that correspond to the client-affecting set of part program instructions is displayed in the editing window; and marking at least one instruction representation of the client-affecting set of instruction representations displayed in the editing window with an indicator to indicate that it corresponds to the first respective element displayed in the client window that was selected by the user.

11. The machine vision inspection system of claim 10, wherein the learn mode user interface is configured such that the client window and the editing window operate according to a set of inter-window auto scroll operations including:

in response to user selection of a first member of the client-affecting set of instruction representations in the editing window, an inter-window auto scroll operation is initiated comprising:

adjusting the results in the client window such that the first respective element corresponding to the selected first member of the client-affecting set of instruction representations is displayed in the client window; and marking the first respective element displayed in the client window with an indicator to indicate that it corresponds to the first member of the client-affecting set of instruction representations selected by the user in the editing window.

12. The machine vision inspection system of claim 11, wherein:

the first respective set of instruction representations corresponding to the first respective set of part program instructions and the client-affecting set of instruction representations corresponding to the client-affecting set of part program instructions are the same respective set of instruction representations corresponding to the same set of part program instructions.

13. The machine vision inspection system of claim 12, wherein the learn mode user interface is further configured such that the results window and the editing window operate according to a set of inter-window auto scroll operations including:

in response to user selection of the first member of the client-affecting set of instruction representations which is also a first member of the first respective set of part program instructions, an inter-window auto scroll operation is initiated comprising:

adjusting the results in the results window such that at least one member of the first respective set of results is displayed in the results window; and marking at least one member of the first respective set of results displayed in the results window with an indicator to indicate that it corresponds to the first member of the client-affecting set of instruction representations which is also the first member of the first respective set of part program instructions selected by the user in the editing window.

14. The machine vision inspection system of claim 1, wherein the machine vision inspection system further comprises:

an editing portion configured such that it is operable to edit a part program, the editing portion comprising an editing execution portion operable to execute previously recorded part program instructions according to an edit mode of execution that is different than the run mode of execution, wherein:

the learn mode is configured such that it is further operable to automatically record respective surrogate data which is associated with a respective set of recorded part program instructions, and at least some respective surrogate data comprises data which results from actual execution of controlled operations corresponding to the associated respective set of recorded part program instructions; and the edit mode of execution comprises a surrogate execution mode wherein during surrogate execution mode of part program instructions represented in the editable part program representation, for at least one set of part program instructions, if respective surrogate data has been previously recorded in association with that set of part program instructions, then at least some members of that set of part program instructions are not executed such that their associated controlled operations are not actually executed, and the respective surrogate data is used in subsequent operation of the surrogate execution mode as a substitute for data that would otherwise result from their associated controlled operations which are not executed.

15. The machine vision inspection system of claim 14, wherein creating a part program comprises modifying a previously recorded part program instruction.

16. The machine vision inspection system of claim 14, wherein the inter-window auto scroll operation that is initiated further comprises:

transferring control to the editing window such that editing operations are immediately facilitated;

selecting in the editing window the at least one instruction that corresponds to the member of the first respective results selected by the user in the results window;

establishing the proper context for editing the selected at least one instruction by beginning the edit mode of execution at a valid context starting location in the part program prior to the selected at least one instruction; and using the surrogate execution mode for executing at least a portion of the part program instructions in order to establish the valid context for editing the selected at least one instruction.

17. The machine vision inspection system of claim 16, wherein the learn mode is configured such that when the valid context is established at the selected at least one instruction, the learn mode user interface is be configured to display a context status indicator proximate to the selected at least one instruction indicated in the part program representation, and the context status indicator is set to indicate that a valid context has been established at the target location.

18. The machine vision inspection system of claim 17, wherein the learn mode is configured such that when the edit mode of execution uses the surrogate execution mode for executing at least a portion of the part program instructions in order to establish the valid context, then the state of the context status indicator is set to a state that specifically indicates that surrogate execution mode has been used to establish the valid context.

\* \* \* \* \*